(12) United States Patent
Bunquin et al.

(10) Patent No.: US 11,857,954 B2
(45) Date of Patent: Jan. 2, 2024

(54) SUPPORTED NANOPARTICLE COMPOSITIONS AND PRECURSORS, PROCESSES FOR MAKING THE SAME AND SYNGAS CONVERSION PROCESSES

(71) Applicant: ExxonMobil Chemical Patents Inc., Baytown, TX (US)

(72) Inventors: Jeffrey C. Bunquin, Houston, TX (US); Joshua J. Willis, Houston, TX (US); Paul F. Keusenkothen, Houston, TX (US); Javier Guzman, Porter, TX (US); Jennifer R. Pena, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 197 days.

(21) Appl. No.: 17/442,710

(22) PCT Filed: Mar. 27, 2020

(86) PCT No.: PCT/US2020/025168
§ 371 (c)(1),
(2) Date: Sep. 24, 2021

(87) PCT Pub. No.: WO2020/205494
PCT Pub. Date: Oct. 8, 2020

(65) Prior Publication Data
US 2022/0176365 A1 Jun. 9, 2022

Related U.S. Application Data

(60) Provisional application No. 62/825,956, filed on Mar. 29, 2019.

(30) Foreign Application Priority Data

Jun. 18, 2019 (EP) .................................. 19180780

(51) Int. Cl.
*B01J 35/00* (2006.01)
*B01J 6/00* (2006.01)
(Continued)

(52) U.S. Cl.
CPC .......... *B01J 35/0013* (2013.01); *B01J 6/001* (2013.01); *B01J 23/8892* (2013.01);
(Continued)

(58) Field of Classification Search
CPC .... B01J 35/0013; B01J 6/001; B01J 23/8892; B01J 35/006; B01J 35/08; B01J 37/0072;
(Continued)

(56) References Cited

U.S. PATENT DOCUMENTS 3,397,154 A * 8/1968 Talsma ................ B01D 53/944
60/299
4,072,600 A 2/1978 Schwartz ..................... 208/120
(Continued)

FOREIGN PATENT DOCUMENTS

CN 106391073 A 2/2017 ............. B01J 27/22
EP 1940739 3/2016 ............. C01B 19/00
(Continued)

OTHER PUBLICATIONS

Chemical and Engineering News, (1985) v.63(5), p. 27.
(Continued)

*Primary Examiner* — Patricia L. Hailey

(57) ABSTRACT

Disclosed are novel supported nanoparticle compositions, precursors, processes for making supported nanoparticle compositions, processes for making catalyst compositions, and processes for converting syngas. The catalyst composition can comprise nanoparticles comprising metal oxide(s), such as manganese cobalt oxide. This disclosure is
(Continued)

particularly useful for converting syngas via the Fischer-Tropsch reactions to make olefins and/or alcohols.

24 Claims, 4 Drawing Sheets

(51) Int. Cl.
| | |
|---|---|
| *B01J 23/889* | (2006.01) |
| *B01J 35/08* | (2006.01) |
| *B01J 37/00* | (2006.01) |
| *B01J 37/02* | (2006.01) |
| *C07C 1/04* | (2006.01) |
| *C07C 29/156* | (2006.01) |

(52) U.S. Cl.
CPC ............ *B01J 35/006* (2013.01); *B01J 35/08* (2013.01); *B01J 37/0072* (2013.01); *B01J 37/0207* (2013.01); *B01J 37/0209* (2013.01); *B01J 37/0215* (2013.01); *C07C 1/0435* (2013.01); *C07C 29/156* (2013.01); *C07C 2523/84* (2013.01)

(58) Field of Classification Search
CPC ................ B01J 37/0207; B01J 37/0209; B01J 37/0215; C07C 1/0435; C07C 29/156; C07C 2523/84
USPC ....... 502/324, 325, 338, 328, 330, 343, 344; 518/713, 715; 977/773, 775, 811
See application file for complete search history.

(56) References Cited

U.S. PATENT DOCUMENTS

| | | | | |
|---|---|---|---|---|
| 4,093,535 | A | 6/1978 | Schwartz | 208/120 |
| 4,313,848 | A | 2/1982 | Scott | 252/418 |
| 4,325,833 | A | 4/1982 | Scott | 252/417 |
| 4,413,573 | A | 11/1983 | Hall et al. | 110/347 |
| 4,588,705 | A * | 5/1986 | Vanderspurt | B01J 35/006 |
| | | | | 502/328 |
| 4,828,680 | A | 5/1989 | Green et al. | 208/120 |
| 4,985,133 | A | 1/1991 | Sapre | 208/78 |
| 4,991,521 | A | 2/1991 | Green et al. | 110/347 |
| 5,162,284 | A | 11/1992 | Soled et al. | 502/324 |
| 6,211,255 | B1 | 4/2001 | Schanke et al. | 518/715 |
| 6,476,085 | B2 | 11/2002 | Manzer et al. | 518/715 |
| 7,128,891 | B1 | 10/2006 | Sun | 423/511 |
| 7,407,572 | B2 | 8/2008 | Steffens et al. | 208/113 |
| 7,485,767 | B2 | 2/2009 | Lattner et al. | 585/639 |
| 7,867,556 | B2 | 1/2011 | Pickett | 427/214 |
| 8,642,496 | B2 * | 2/2014 | Xia | B01J 23/626 |
| | | | | 429/484 |
| 8,987,163 | B2 | 3/2015 | Galvis et al. | 502/107 |
| 9,422,204 | B2 | 8/2016 | Karim et al. | C07C 1/0435 |
| 9,486,785 | B2 | 11/2016 | Karim et al. | B01J 23/8892 |
| 9,545,620 | B2 | 1/2017 | Karim et al. | B01J 23/8892 |
| 9,669,393 | B2 | 6/2017 | Karim et al. | B01J 27/0515 |
| 9,695,365 | B2 | 7/2017 | Bashir et al. | C10G 2/332 |
| 9,761,884 | B2 | 9/2017 | Atwan et al. | |
| 2003/0138373 | A1 * | 7/2003 | Graham | C10L 1/328 |
| | | | | 423/652 |
| 2005/0130837 | A1 * | 6/2005 | Hoek | B01J 23/75 |
| | | | | 502/325 |
| 2006/0133990 | A1 | 6/2006 | Hyeon et al. | 423/622 |
| 2009/0143493 | A1 * | 6/2009 | Geerlings | C10G 2/332 |
| | | | | 518/715 |
| 2010/0184588 | A1 * | 7/2010 | Rinaldi | B01J 23/66 |
| | | | | 977/773 |
| 2013/0046033 | A1 * | 2/2013 | Ferrini | C07C 1/044 |
| | | | | 518/719 |
| 2013/0168228 | A1 * | 7/2013 | Ozin | C25B 3/25 |
| | | | | 977/773 |
| 2013/0274093 | A1 * | 10/2013 | Woodfield | B01J 23/8913 |
| | | | | 502/332 |
| 2015/0158785 | A1 | 6/2015 | Soultanidis et al. | C07C 1/22 |
| 2017/0354962 | A1 | 12/2017 | D'Souza et al. | |

FOREIGN PATENT DOCUMENTS

| | | | | |
|---|---|---|---|---|
| EP | 2490989 | | 2/2020 | ............... C07C 1/04 |
| WO | WO-2010049714 A1 * | | 5/2010 | .......... B01J 23/8896 |
| WO | WO2017/173791 | | 10/2017 | ............... B01J 23/75 |
| WO | WO-2019068110 A1 * | | 4/2019 | ............... B01J 23/38 |
| WO | WO2020/205500 | | 10/2020 | ............... B01J 23/24 |
| WO | PCT/US21/045322 | | 8/2021 | |

OTHER PUBLICATIONS

Gonzalez-Carballo, J. M. et al. (2016) "Synthesis of Cobalt Nanodumbells and their Thermal Stability under H2, H2/CO and O2 Atmospheres," *Materials Characterization*, v.118(25), pp. 519-526.

Werner, S. et al. (2014) "Synthesis and Characterization of Supported Cobalt-Manganese Nanoparticles as Model Catalysts for Fischer-Tropsch Synthesis," *Chemcatchem*, v.6(10), pp. 2881-2888.

Zhang, H. et al. (2006) "Size-Dependent X-Ray Photoelectron Spectroscopy and Complex Magnetic Properties of $CoMn_2O_4$ Spinel Nanocrystals," *Nanotechnology*, v. 17(5), pp. 1384-1390.

* cited by examiner

SUPPORTED NANOPARTICLE COMPOSITIONS AND PRECURSORS, PROCESSES FOR MAKING THE SAME AND SYNGAS CONVERSION PROCESSES

CROSS-REFERENCE TO RELATED APPLICATIONS

This application is a national stage filing of Patent Cooperation Treaty Application No. PCT/US2020/025168 filed Mar. 27, 2020, which claims the benefit of U.S. Provisional Application No. 62/825,956, filed Mar. 29, 2019 and European Patent Application No. 19180780.9, filed Jun. 18, 2019, the disclosures of 62/825,956 and 19180780.9 are incorporated herein by reference.

FIELD

The present disclosure relates to supported nanoparticle compositions, catalyst compositions, processes for making supported nanoparticle compositions, processes for making catalyst compositions, and processes for converting syngas. This disclosure is useful, e.g. in production of supported metal oxide nanoparticles and converting syngas into olefins and/or alcohols, especially C2-O5 olefins and C1-O5 alcohols.

BACKGROUND

Synthesis gas (syngas) is a mixture of hydrogen and carbon monoxide generated from the upgrading of chemical feedstocks such as natural gas and coal. Syngas has been used industrially for the production of value-added chemicals including chemical intermediates, such as olefins, alcohols, and fuels. Fischer-Tropsch catalysis is one route for syngas conversion to value-added products. Generally, Fischer-Tropsch catalysis involves the use of iron and cobalt catalysts for the production of gasoline range products for transportation fuels, heavy organic products including distillates used in diesel fuels, and high purity wax for a range of applications including food production.

Similar catalysts can be used for the production of value-added chemical intermediates including olefins and alcohols that can be used, for example, for the production of polymers and fuels. Often the production of value-added chemicals includes the production of saturated hydrocarbons, such as paraffins. The selectivity of Fischer-Tropsch catalysts towards production of value-added chemical intermediates may be adjusted by addition of promoters comprising group 1 and group 2 cations and transition metals. Fischer-Tropsch catalysts have been prepared as metal oxides or sulfides of iron and cobalt. The iron and cobalt catalysts are frequently supported on solid carriers comprising oxides such as alumina, silica, or various clays or on carbonaceous materials. Fischer-Tropsch catalysts have been used to produce hydrocarbons in the gasoline range and lighter hydrocarbons.

The development of monodisperse and crystalline nanoparticles of metals, alloys, metal oxides and multi-metallic oxides have been sought after for not only their fundamental scientific interests, but also many potential technological and practical applications including catalysis.

Supported heterogeneous catalysts may be composed of an active phase nanoparticle and possible secondary and tertiary promoter nanoparticles supported on a high surface area support. Supported heterogeneous catalysts may be valuable to a wide variety of catalytic reactions, such as combustion, hydrogenation, or Fischer-Tropsch synthesis. Many reactions are structure sensitive such that the activity, stability, and selectivity are strongly dependent on the crystal structure, phase, and size of the supported active phase nanoparticles. Current industrial techniques for supported catalyst synthesis are unable to effectively control the active phase size, and shape with high precision (<20% standard deviation in size), as well as, successfully incorporate secondary and tertiary metals into the active phase uniformly for promotion of activity, stability, and selectivity.

Advances in colloidal chemistry have resulted in the synthesis of metal and metal oxide nanoparticles. However, previous synthetic methods do not produce nanoparticles of uniform size and/or shape, are not scalable for industrial application, involve complicate procedures, require (e.g., not merely optional) the use of obscure and/or exotic precursors, require (e.g., not merely optional) addition of surfactants, produce nanoparticles of low crystallinity, and require (e.g., not merely optional) the use of multiple reaction vessels.

There is a need for improved catalyst compositions for use in syngas conversion, particularly Fischer-Tropsch conversion of syngas into light alcohols and olefins with low methane formation. Furthermore, there remains a need for a convenient route to making metal nitrides and carbides and mixed metal nitrides and carbides from readily available starting materials. There is a need for a scalable and simple synthesis of size, shape, and composition controlled mixed metal oxide nanoparticles as supported catalyst precursors for a variety of reactions.

References for citing in an information disclosure statement (37 C.F.R 1.97(h)): U.S. Pat. Nos. 5,162,284; 7,128,891; 7,407,572; 7,867,556; 8,987,163; 9,422,204; 9,486,785; 9,545,620 9,669,393; 9,695,365; U.S. Patent Publication Nos. 2006/0133990, 2015/0158785; Patent Cooperation Treaty Publication WO2017/173791; China Patent No. 106391073A.

SUMMARY

One possible solution is pre-forming size-, shape-, and composition-controlled nanoparticles and subsequently dispersing the nanoparticles onto support materials. It has been discovered that metal oxide nanoparticles can be produced that have one or more of the following characteristics: high crystallinity, uniform particle size, uniform particle shape, uniform distribution of metals within a nanoparticle, dispersability in hydrophobic solvents and on supports, and control of both size and shape. Furthermore, it has been discovered that supported metal oxide nanoparticles can be used in synthesis of light hydrocarbons from syngas.

A first aspect of this disclosure relates to a supported nanoparticle composition comprising a support and a plurality of nanoparticles, where each nanoparticle comprises a kernel, the kernels have an average particle size from 4 to 100 nm and a particle size distribution of no greater than 20%; the kernels comprise oxygen, a metal element M1, optionally sulfur, optionally phosphorus, optionally a metal element M2, and optionally a third metal element M3, where M1 is selected from Mn, Fe, Co, and combination of two or more thereof, M2 is selected from Ni, Zn, Cu, Mo, W, Ag, and combinations thereof, and M3 is selected from Y, Sc, alkaline metals, the lanthanides, group 13, 14, and 15 metal elements, and combinations thereof, and the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$.

A Second aspect of this disclosure relates to processes for making a supported nanoparticle composition, the process comprises:

providing a nanoparticle dispersion system comprising a liquid medium and a plurality of nanoparticles distributed therein, where each nanoparticle comprises a kernel, the kernels have an average particle size from 4 to 100 nm and a particle size distribution, expressed as a percentage of the standard deviation of the particle size relative to the average particle size, of no greater than 20%, as determined by small angle X-ray scattering ("SAXS") and transmission electron microscopy ("TEM") image analysis; the kernels comprise oxygen, a metal element M1, optionally sulfur, optionally phosphorus, optionally a second metal element M2, and optionally a third metal element M3, where M1 is selected from Mn, Fe, Co, and combination of two or more thereof, M2 is selected from Ni, Zn, Cu, Mo, W, Ag, and combinations thereof, and M3 is selected from Y, Sc, alkaline metals, the lanthanides, group 13, 14, and 15 elements, and combinations thereof, and the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$; and (II) disposing a quantity of the nanoparticle dispersion on a support to obtain a first support/nanoparticle mixture.

A third aspect of this disclosure relates to a process for converting syngas, the process comprising contacting a feed comprising syngas with a supported nanoparticle composition in a conversion reactor under conversion conditions to produce a conversion product mixture effluent.

DETAILED DESCRIPTION

Figure 1:
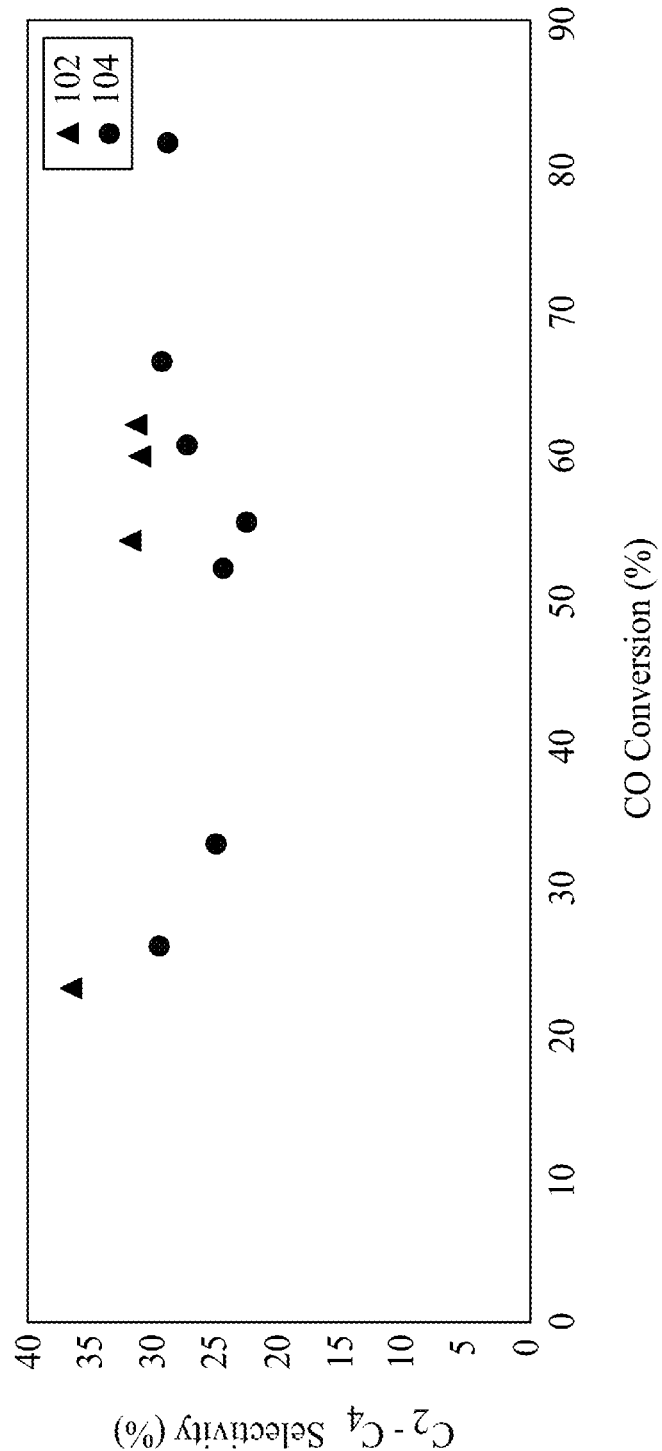
FIG. 1 is a graph showing C2-C4 selectivity versus CO conversion rate in syngas conversion, according to an embodiment.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments comprising "a metal" include embodiments comprising one, two, or more metals, unless specified to the contrary or the context clearly indicates only one metal is included.

For the purposes of this disclosure, the nomenclature of elements is pursuant to the version of Periodic Table of Elements as described in CHEMICAL AND ENGINEERING NEWS, 63(5), pg. 27 (1985). Abbreviations for atoms are as given in the periodic table (Li=lithium, for example).

The following abbreviations may be used herein for the sake of brevity: RT is room temperature (and is 23° C. unless otherwise indicated), kPag is kilopascal gauge, psig is pound-force per square inch gauge, psia is pound-force per square inch absolute, and WHSV is weight hourly space velocity, and GHSV is gas hourly space velocity. Abbreviations for atoms are as given in the periodic table (Co=cobalt, for example).

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure. Additionally, they do not exclude impurities and variances normally associated with the elements and materials used. "Consisting essentially of" a component in this disclosure can mean, e.g., comprising, by weight, at least 80 wt %, of the given material, based on the total weight of the composition comprising the component.

For purposes of this disclosure and claims thereto, the term "substituted" means that a hydrogen atom in the compound or group in question has been replaced with a group or atom other than hydrogen. The replacing group or atom is called a substituent. Substituents can be, e.g., a substituted or unsubstituted hydrocarbyl group, a heteroatom, a heteroatom-containing group, and the like. For example, a "substituted hydrocarbyl" is a group derived from a hydrocarbyl group made of carbon and hydrogen by substituting at least one hydrogen in the hydrocarbyl group with a non-hydrogen atom or group. A heteroatom can be nitrogen, sulfur, oxygen, halogen, etc.

The terms "hydrocarbyl," "hydrocarbyl group," or "hydrocarbyl radical" interchangeably mean a group consisting of carbon and hydrogen atoms. For purposes of this disclosure, "hydrocarbyl radical" is defined to be C1-C100 radicals, that may be linear, branched, or cyclic, and when cyclic, aromatic or non-aromatic.

The term melting point (mp) refers to the temperature at which solid and liquid forms of a substance can exist in equilibrium at 760 mmHg.

The term boiling point (bp) refers to the temperature at which liquid and gas forms of a substance can exist in equilibrium at 760 mmHg.

"Soluble" means, with respect to a given solute in a given solvent at a given temperature, at most 100 mass parts of the solvent is required to dissolve 1 mass part of the solute under a pressure of 1 atmosphere. "Insoluble" means, with respect to a given solute in a given solvent at a given temperature, more than 100 mass parts of the solvent is required to dissolve 1 mass part of the solute under a pressure of 1 atmosphere.

The term "branched hydrocarbon" means a hydrocarbon comprising at least 4 carbon atoms and at least one carbon atom connecting to three carbon atoms.

The term "olefinicity" refers to the molar ratio of the sum of olefins to the sum of paraffins detected. The olefinicity increases when the olefin/paraffin molar ratio increases. The olefinicity decreases when the olefin/paraffin molar ratio decreases.

The terms "alkyl," "alkyl group," and "alkyl radical" interchangeably mean a saturated monovalent hydrocarbyl group. A "cyclic alkyl" is an alkyl comprising at least one cyclic carbon chain. An "acyclic alkyl" is an alkyl free of any cyclic carbon chain therein. A "linear alkyl" is an acyclic alkyl having a single unsubstituted straight carbon chain. A "branched alkyl" is an acyclic alkyl comprising at least two carbon chains and at least one carbon atom connecting to three carbon atoms. Alkyl groups can comprise, for example, methyl, ethyl, n-propyl, isopropyl, n-butyl, isobutyl, sec-butyl, tert-butyl, pentyl, iso-amyl, hexyl, octyl, cyclopropyl, cyclobutyl, cyclopentyl, cyclohexyl, cyclooctyl, and the like including their substituted analogues.

The term "Cn" compound or group, where n is a positive integer, means a compound or a group comprising carbon atoms therein at the number of n. Thus, a "Cm to Cn" alkyl means an alkyl group comprising carbon atoms therein at a number in a range from m to n, or a mixture of such alkyl groups. Thus, a C1-C3 alkyl means methyl, ethyl, n-propyl, or 1-methylethyl-. The term "Cn+" compound or group, where n is a positive integer, means a compound or a group comprising carbon atoms therein at the number of equal to or greater than n. The term "Cn-" compound or group, where n is a positive integer, means a compound or a group comprising carbon atoms therein at the number of equal to or lower than n.

The term "conversion" refers to the degree to which a given reactant in a particular reaction (e.g., dehydrogenation, hydrogenation, etc.) is converted to products. Thus 100% conversion of carbon monoxide means complete consumption of carbon monoxide, and 0% conversion of carbon monoxide means no measurable reaction of carbon monoxide.

The term "selectivity" refers to the degree to which a particular reaction forms a specific product, rather than another product. For example, for the conversion of syngas, 50% selectivity for C1-C4 alcohols means that 50% of the products formed are C1-C4 alcohols, and 100% selectivity for C1-C4 alcohols means that 100% of the products formed are C1-C4 alcohols. The selectivity is based on the product formed, regardless of the conversion of the particular reaction.

The term "nanoparticle" means a particle having a largest dimension in the range from 0.1 to 500 nanometers.

The term "long-chain" means comprising a straight carbon chain having at least 8 carbon atoms excluding any carbon atoms in any branch that may be connected to the straight carbon chain. Thus, n-octane and 2-octain are long-chain alkanes, but 2-methylheptane is not. A long-chain organic acid is an organic acid comprising a straight carbon chain having at least 8 carbon atoms excluding any carbon atoms in any branch that may be connected to the straight carbon chain. Thus, octanoic acid is a long-chain organic acid, but 6-methylheptanoic acid is not.

The term "organic acid" means an organic Bronsted acid capable of donating a proton. Organic acids include, carboxylic acids of any suitable chain length; carbon containing sulfinic, sulfonic, phosphinic, and phosphonic acids; hydroxamic acids, and in some embodiments, amidines, amides, imides, alcohols, and thiols.

The term "surfactant" means a material capable of reducing the surface tension of a liquid in which it is dissolved. Surfactants can find use in, for example, detergents, emulsifiers, foaming agents, and dispersants.

Detailed description of the nanoparticles and catalyst compositions of this disclosure, including the composition comprising nanoparticles of the first aspect, the process for producing nanoparticles of the second aspect, and the catalyst composition of the third aspect of this disclosure, is provided below.

Kernel Characteristics

A nanoparticle may be present as a discreet particle dispersed in a media such as a solvent, e.g., a hydrophobic solvent such as toluene in certain embodiments. Alternatively, a nanoparticle may be stacked next to a plurality of other nanoparticles in the composition of this disclosure. A nanoparticle in the nanoparticle composition of this disclosure comprises a kernel which are observable under a transmission electron microscope. The nanoparticle may in certain embodiments further comprises one or more long-chain groups attached to the surface thereof. Alternatively, a nanoparticle may consist essentially of, or consist entirely of a kernel only.

A kernel in a nanoparticle can have a largest dimension in a range of from 4 nanometers to 100 nanometers. Kernels may have a near spherical or elongated shape (e.g. rod-shaped). Kernels that are elongated may have an aspect ratio of from 1 to 50, such as from 1.5 to 30, from 2 to 20, from 2 to 10, or from 3 to 8. The aspect ratio is the length of a longer side of the kernel divided by the length of a shorter side of the kernel. For example, a rod-shaped kernel of diameter 4 nm and length of 44 nanometers has an aspect ratio of 11.

The kernels of the nanoparticles in the nanoparticle compositions of this disclosure may have a particle size distribution of 20% or less. The particle size distribution is expressed as a percentage of the standard deviation of the particle size relative to the average particle size. For example, a plurality of kernels that have an average size of 10 nanometers and a standard deviation of 1.5 nanometers has a particle size distribution of 15%. The kernels of the nanoparticles in the nanoparticle compositions of this disclosure may have an average particle size of from 4 to 100 nm, such as 4 to 35 nm, or 4 to 20 nm.

Particle size distribution is determined by Transmission Electron Microscopy ("TEM") measurement of nanoparticles deposited on a flat solid surface.

The kernels of the nanoparticles in the nanoparticle compositions of this disclosure may be crystalline, semi-crystalline, or amorphous in nature.

Kernels are composed of at least one metal element. The at least one metal may be selected from groups Mn, Fe, Co, Zn, Cu, Mo, W, Ag, Y, Sc, alkaline metals, the lanthanide series, group 13, 14, and 15, and combinations thereof. Where the at least one metal element comprises two or more metals, the metals may be designated as M1, M2, and M3, according to the number of metal elements. M1 may be selected from manganese, iron, cobalt, combinations of iron and cobalt at any proportion, combinations of iron and manganese at any proportion, combinations of cobalt with manganese at any proportion, and combinations of iron, cobalt, and manganese at any proportion. In specific embodiments, M1 is a single metal of manganese, cobalt, or iron. Where M1 comprises a binary mixture/combination of cobalt and manganese, cobalt may be present at a higher molar proportion than manganese. Where M1 comprises a binary mixture/combination of iron and manganese, iron may be present at a higher molar proportion than manganese. Without intending to be bound by a particular theory, it is believed that the presence of M1 provides at least a portion of the catalytic effect of the catalyst composition of the third aspect of this disclosure.

M2 may be selected from nickel, zinc, copper, molybdenum, tungsten, silver, and combinations thereof. Without intending to be bound by a particular theory, it is believed that the presence of M2 promotes the catalytic effect of M1 in the supported nanoparticle compositions of the first aspect of this disclosure.

The presence of M3 in the compositions of this disclosure is optional. If present, M3 may be selected from Y, Sc, lanthanides, and metal elements of Groups 1, 13, 14, or 15, and any combination(s) and mixture(s) of two or more thereof at any proportion. In certain embodiments, M3 is selected from aluminum, gallium, indium, thallium, scandium, yttrium, and the lanthanide series, and combination thereof. In some embodiments, M3 is selected from gallium, indium, scandium, yttrium, and lanthanides, and combinations thereof. Preferred lanthanide are: La, Ce, Pr, Nd, Gb, Dy, Ho, Er, and combinations thereof. Without intending to be bound by a particular theory, it is believed the presence of metal M3 can promote the catalyst effect of the catalyst compositions of the third aspect of this disclosure.

The kernels can further comprise oxygen in the form of, e.g., a metal oxide. The presence of a metal oxide can be indicated by the XRD graph of the catalyst composition. By a "metal oxide," it is meant to include oxide of a single metal, or a combination of two or more metals M1, M2, and/or M3. Suitably the kernel may comprise an oxide of a single metal, or a combination of two or more metals of M1, and/or M2. Suitably the kernel may comprise an oxide of a single metal, or a combination of two or more metals of M1. In at least one embodiment, the catalytic component may comprise one or more of iron oxide, cobalt oxide, manganese oxide, (mixed iron cobalt) oxide, (mixed iron manganese) oxide, mixed (cobalt manganese) oxide, and mixed (cobalt, iron, and manganese) oxide. In at least one embodiment, the kernel may comprise an oxide of a single metal, or a combination of two or more metals of M2 (e.g., yttrium and the lanthanides). The kernel may comprise an oxide of a metal mixture comprising an M1 metal and an M2 metal. The identification of the presence of an oxide phase in a nanoparticle can be conducted by comparing the XRD data of the nanoparticle against an XRD peak database of oxides, such as those available from International Center for Diffraction Data ("ICDD").

The kernel compositions of this disclosure may optionally comprise sulfur. Without intending to be bound by a particular theory, in certain embodiments, the presence of sulfur can promote the catalytic effect of the catalyst composition created from the nanoparticle compositions comprising kernels. The sulfur may be present as a sulfide, sulfate, or other sulfur-containing compound of one or more metals of M1, M2, and/or M3.

The kernel compositions of this disclosure may optionally comprise phosphorus. Without intending to be bound by a particular theory, in certain embodiments, the presence of phosphorus can promote the catalytic effect of the catalyst composition created from the nanoparticle compositions comprising kernels. The phosphorus may be present as a phosphide of one or more metals of M1, M2, and/or M3.

In specific embodiments, the kernel of a nanoparticle composition of this disclosure consists essentially of M1, M2, M3, oxygen, optionally sulfur, and optionally phosphorus e.g., comprising ≥85, or ≥90, or ≥95, or ≥98, or even ≥99 wt % of M1, M2, M3, oxygen, optionally sulfur, and optionally phosphorus based on the total weight of the kernel.

The molar ratios of M2 to M1 ("r1"), M3 to M1 ("r2"), oxygen to M1 ("r3"), sulfur to M1 ("r4"), and phosphorus to M1 ("r5"), in the kernel of a nanoparticle composition of this disclosure are calculated from the aggregate molar amounts of the elements in question. Thus, if M1 is a combination/mixture of two or more metals, the aggregate molar amount of all metals of M1 is used for calculating the ratios. If M2 is a combination/mixture of two or more metals, the aggregate molar amounts of all metals M2 is used for calculating the ratio r1. If M3 is a combination/mixture of two or more metals, the aggregate molar amounts of all metals M3 is used for calculating the ratio r2.

The molar ratio of M2 to M1 in the kernel of a nanoparticle composition of this disclosure, r1, can be from r1a to r1b, where r1a and r1b can be, independently, e.g., 0, 0.05, 0.1, 0.2, 0.3, 0.4, 0.5, 0.6, 0.7, 0.8, 0.9, 1, 1.1, 1.2, 1.3, 1.4 or 1.5, as long as r1a<r1b. In some embodiments, r1a=0, r1b=2; such as r1a=0, r1b=0.5; or r1a=0.05, r1b=0.5. In at least one embodiment, r1 is in the vicinity of 0.5 (e.g., from 0.45 to 0.55), meaning that M1 is present in the kernel at substantially twice the molar amount of M2.

The molar ratio of M3 to M1 in the kernel of a nanoparticle compositions of this disclosure, r2, can be from r2a to r2b, where r2a and r2b can be, independently, e.g., 0, 0.005, 0.01, 0.05, 0.1, 0.2, 0.3, 0.4, or 0.5, as long as r2a≤r2b. In some embodiments, r2a=0, r2b=5; such as r2a=0.005, r2b=0.5. Thus M3, if present, is at a substantially lower molar amount than M1.

The molar ratio of oxygen to M1 in the kernel of a nanoparticle composition of this disclosure, r3, can be from r3a to r3b, where r3a and r3b can be, independently, e.g., 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5, as long as r3a≤r3b. In some embodiments, r3a=0.05, r3b=5; such as r3a=0.5, r3b=4; or r3a=1, r3b=3.

The molar ratio of sulfur to M1 in the kernel of a nanoparticle composition of this disclosure, r4, can be from r4a to r4b, where r4a and r4b can be, independently, e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5, as long as r4a≤r4b. In some embodiments, r4a=0, r4b=5; such as r4a=0, r4b=2.

The molar ratio of phosphorus to M1 in the kernel of a nanoparticle composition of this disclosure, r5, can be from r5a to r5b, where r5a and r5b can be, independently, e.g., 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5, as long as r5a≤r5b. In some embodiments, r5a=0, and r5b=5; such as r5a=0 and r5b=2.

In specific embodiments, the metal(s) M1 can be distributed substantially homogeneously in the kernel. Additionally and/or alternatively, the metal(s) M2 can be distributed substantially homogeneously in the kernel. Additionally and/or alternatively, the metal(s) M3 can be distributed substantially homogeneously in the kernel. Additionally and/or alternatively, oxygen can be distributed substantially homogeneously in the kernel. Still additionally and/or alternatively, sulfur can be distributed substantially homogeneously in the kernel. Additionally and/or alternatively, phosphorus can be distributed substantially homogeneously in the kernel.

It is highly advantageous that the metal oxide(s) are highly dispersed in the kernel. The metal oxide(s) can be substantially homogeneously distributed in the kernel, resulting in a highly dispersed distribution, which can contribute to a high catalytic activity of the catalyst composition comprising nanoparticle compositions that comprise kernels.

The nanoparticle composition of this disclosure may comprise or consist essentially of the kernel of this disclosure, e.g., comprising ≥85, or ≥90, or ≥95, or ≥98, or even ≥99 wt % of the kernel, based on the total weight of the nanoparticle composition. The nanoparticle composition of the present disclosure may comprise long-chain hydrocarbyl groups disposed on (e.g. attached to) the kernel.

Nanoparticle Formation

The nanoparticle composition, of this disclosure may be produced from a first dispersion system at a first temperature (T1). A first dispersion system comprises a long-chain hydrocarbon solvent, a salt of at least one long-chain organic acid and the at least one metal element, optionally sulfur or an organic sulfur compound (which can be soluble in the long-chain hydrocarbon solvent), and optionally an organic phosphorus compound (which can be soluble in the long-chain hydrocarbon solvent). The salt of at least one long-chain organic acid and the at least one metal element may be formed in situ with a salt of a second organic acid and the at least one metal element, and a long-chain organic acid The T1 may comprise temperatures from T1a to T1b, where T1a and T1b can be, independently, e.g., 0, RT, 35, 40, 45, 50, 75, 100, 125, 150, 175, 200, 225, 250, 275, or 300° C., as long as T1a<T1b, such as T1a=RT, T1b=250° C.; or T1a=35° C., T1b=150° C. The first temperature may be maintained for from 10 min to 100 hours, such as from 10 min to 10 hours, 10 minutes to 5 hours, 10 minutes to 3 hours, or 10 minutes to 2 hours. The first dispersion system may be held under inert atmosphere or under pressure reduced below atmospheric pressure. For example, the first dispersion system may be maintained under flow of nitrogen or argon, and alternatively, may be attached to a vacuum reducing the pressure to less than 760 mmHg, such as less than 400 mmHg, less than 100 mmHg, less than 50 mmHg, less than 30 mmHg, less than 20 mmHg, less than 10 mmHg, or less than 5 mmHg. The choice of maintaining the first dispersion system under flow of inert gas versus reduced pressure may affect the size of the nanoparticles produced. Without being limited by theory, it is possible that a first dispersion system under reduced pressure has fewer contaminants and byproducts than if it was maintained under flow of inert gas and the fewer contaminants may allow for formation of smaller nanoparticles. In some embodiments, maintaining the first dispersion system under reduced pressure may decrease nanoparticle size without affecting particle size distribution as compared to maintaining the first dispersion system under flow of inert gas. In other embodiments, maintaining the first dispersion system under flow of inert gas may increase nanoparticle size without affecting particle size distribution as compared to maintaining the first dispersion system under reduced pressure.

The long-chain hydrocarbon solvent may comprise saturated and unsaturated hydrocarbons, aromatic hydrocarbons, and hydrocarbon mixture(s).

Some example saturated hydrocarbons suitable for use as the long-chain hydrocarbon solvent are C12+ hydrocarbons, such as C12 to C24, C14 to C24, C16 to C22, C16 to C20, C16 to C18 hydrocarbons, such as n-dodecane (mp −10° C., bp 214° C. to 218° C.), n-tridecane (mp −6° C., bp 232° C. to 236° C.), n-tetradecane (mp 4° C. to 6° C., bp 253° C. to 257° C.), n-pentadecane (mp 10° C. to 17° C., bp 270° C.), n-hexadecane (mp 18° C., bp 287° C.), n-heptadecane (mp 21° C. to 23° C., bp 302° C.), n-octadecane (mp 28° C. to 30° C., bp 317° C.), n-nonadecane (mp 32° C., bp 330° C.), n-icosane (mp 36° C. to 38° C., bp 343° C.), n-henicosane (mp 41° C., bp 357° C.), n-docosane (mp 42° C., bp 370° C.), n-tricosane (mp 48° C. to 50° C., bp 380° C.), n-tetracosane (mp 52° C., bp 391° C.), or mixture(s) thereof.

Some example unsaturated hydrocarbons suitable for use as the long-chain hydrocarbon solvent include C12+ unsaturated unbranched hydrocarbons, such as C12 to C24, C14 to C24, C16 to C22, C16 to C20, C16 to C18 unsaturated unbranched hydrocarbons (the double-bond may be cis or trans and located in any of the 1, 2, 3, 4, 5, 6, 7, 8, 9, 10, 11, or 12 positions), such as 1-dodecene (mp −35° C., bp 214° C.), 1-tridecene (mp −23° C., bp 232° C. to 233° C.), 1-tetradecene (mp −12° C., bp 252° C.), 1-pentadecene (mp −4° C., bp 268° C. to 239° C.), 1-hexadecene (mp 3° C. to 5° C., bp 274° C.), 1-heptadecene (mp 10° C. to 11° C., bp 297° C. to 300° C.), 1-octadecene (mp 14° C. to 16° C., bp 315° C.), 1-nonadecene (mp 236° C., bp 329° C.), 1-icosene (mp 26° C. to 30° C., bp 341° C.), 1-henicosene (mp 33° C., bp 353° C. to 354° C.), 1-docosene (mp 36° C. to 39° C., bp 367° C.), 1-tricosene (bp 375° C. to 376° C.), 1-tetracosene (bp 380° C. to 389° C.), trans-2-dodecene (mp −22° C., bp 211° C. to 217° C.), trans-6-tridecene (mp −11° C., bp 230° C. to 233° C.), cis-5-tridecene (mp −11° C. to −10° C., bp 230° C. to 233° C.), trans-2-tetradecene (mp 1° C. to 3° C., bp 250° C. to 253° C.), trans-9-octadecene (mp 23° C. to 25° C., bp 311° C. to 318° C.), cis-12-tetracosene (mp 96° C. to 97° C., bp 385° C. to 410° C.), or mixture(s) thereof. In some embodiments, the long-chain hydrocarbon solvent is 1-octadecene.

Aromatic hydrocarbons suitable for use as the long-chain hydrocarbon may comprise any of the above alkanes and alkenes where a hydrogen atom is substituted for a phenyl, naphthyl, anthracenyl, pyrrolyl, pyridyl, pyrazyl, pyrimidyl, imidazolyl, furanyl, or thiophenyl substituent.

Hydrocarbon mixtures suitable for use as the long-chain hydrocarbon may comprise mixtures with sufficiently high boiling points such that at least partial decomposition of the metal salts may occur upon heating below or at the boiling point of the mixture. Suitable mixtures may include: kerosene, lamp oil, gas oil, diesel, jet fuel, or marine fuel.

The long-chain organic acid may comprise any suitable organic acid with a long-chain, such as saturated carboxylic acids, mono unsaturated carboxylic acids, polyunsaturated carboxylic acids, saturated or unsaturated sulfonic acids, saturated or unsaturated sulfinic acids, saturated or unsaturated phosphonic acids, saturated or unsaturated phosphinic acids.

The long-chain organic acid may be selected from C12+ organic acids, such as C12 to C24, C14 to C24, C16 to C22, C16 to C20, or C16 to C18 organic acids. In some embodiments, the organic acid is a fatty acid, for example: caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, behenic acid, lignoceric acid, myristoleic acid, palmitoleic acid, sapienic acid, oleic acid, elaidic acid, vaccenic acid, petroselenic acid, linoleic acid, linoelaidic acid, α-linolenic acid, γ-linolenic acid, stearidonic acid, gondoic acid, paullinic acid, gondoic acid, gadoleic acid, arachidonic acid, eicosenoic acid, eicosapentaenoic acid, brassidic acid, erucic acid, adrenic acid, osbond acid, clupanodonic acid, docosahexaenoic acid, nervonic acid, colneleic acid, colnelenic acid, etheroleic acid, or etherolenic acid.

The long-chain organic acid may be selected from C12+ unsaturated acids, such as C12 to C24, C14 to C24, C16 to C22, C16 to C20, C16 to C18 unsaturated acids, such as myristoleic acid, palmitoleic acid, sapienic acid, vaccenic acid, petroselenic acid, oleic acid, elaidic acid, paullinic acid, gondoic acid, gadoleic acid, eicosenoic acid, brassidic acid, erucic acid, nervonic acid.

The long-chain organic acid may be selected from myristoleic acid, palmitoleic acid, cis-vaccenic acid, paullinic acid, oleic acid, gondoic acid, or gadoleic acid. In some embodiments, the long-chain organic acid is oleic acid.

The long-chain organic acids used to prepare the metal salts may be similar in chain length to the long-chain hydrocarbon solvent, such as where the long-chain organic acid and the long-chain hydrocarbon do not differ in numbers of carbon atoms by more than 4, such as 3 or less, or 2 or less. For example, if metal oleate salts are used, then suitable long-chain hydrocarbon solvents may include: 1-heptadecene, 1-octadecene, 1-nonadecene, trans-2-octadecene, cis-9-octadecene or mixture(s) thereof.

Metal salts of the long-chain organic acid comprise the salt of (i) at least one metal selected from groups 1, 2, 3, 4, 5, 6, 11, 12, 13, 14, and 15, Mn, Fe, Co, Ni, or W, and combinations thereof; and (ii) a long-chain organic acid. As salts, the metals may be in a 2+, 3+, 4+, or 5+ oxidation state forming Metal (II), Metal (III), Metal (IV), and Metal (V) complexes with the long-chain organic acid. If an oxidation state is not specified the metal salt may comprise Metal (II), Metal (III), Metal (IV), and Metal (V) complexes.

The metal salts of long-chain organic acids may be M1 metal salts comprising the salt of an M1 metal and a long-chain organic acid. The metal salts of long-chain organic acids may be M2 metal salts comprising the salt of an M2 metal and a long-chain organic acid. The metal salts of long-chain organic acids may be M3 metal salts comprising the salt of an M3 metal and a long-chain organic acid. M1 metal salts, M2 metal salts, and M3 metal salts need not contain the same long-chain organic acid. Furthermore, M1 metal salts, M2 metal salts, and M3 metal salts may be formed in situ with a salt of a second organic acid and the M1, M2, or M3 metal element, and a long-chain organic acid.

In at least one embodiments, the M1 metal salt is selected from cobalt myristoleate, cobalt palmitoleate, cobalt cis-vaccenate, cobalt paullinate, cobalt oleate, cobalt gondoate, cobalt gadoleate, iron myristoleate, iron palmitoleate, iron cis-vaccenate, iron paullinate, iron oleate, iron gondoate, iron gadoleate, manganese myristoleate, manganese palmitoleate, manganese cis-vaccenate, manganese paullinate, manganese oleate, manganese gondoate, or manganese gadoleate.

In at least one embodiments, the M2 metal salt is selected from nickel myristoleate, nickel palmitoleate, nickel cis-vaccenate, nickel paullinate, nickel oleate, nickel gondoate, nickel gadoleate, zinc myristoleate, zinc palmitoleate, zinc cis-vaccenate, zinc paullinate, zinc oleate, zinc gondoate, zinc gadoleate, copper myristoleate, copper palmitoleate, copper cis-vaccenate, copper paullinate, copper oleate, copper gondoate, copper gadoleate, molybdenum myristoleate, molybdenum palmitoleate, molybdenum cis-vaccenate, molybdenum paullinate, molybdenum oleate, molybdenum gondoate, molybdenum gadoleate, tungsten myristoleate, tungsten palmitoleate, tungsten cis-vaccenate, tungsten paullinate, tungsten oleate, tungsten gondoate, tungsten gadoleate, silver myristoleate, silver palmitoleate, silver cis-vaccenate, silver paullinate, silver oleate, silver gondoate, or silver gadoleate.

In at least one embodiment, the M3 metal salt is selected from gallium myristoleate, gallium palmitoleate, gallium cis-vaccenate, gallium paullinate, gallium oleate, gallium gondoate, gallium gadoleate, indium myristoleate, indium palmitoleate, indium cis-vaccenate, indium paullinate, indium oleate, indium gondoate, indium gadoleate, scandium myristoleate, scandium palmitoleate, scandium cis-vaccenate, scandium paullinate, scandium oleate, scandium gondoate, scandium gadoleate, yttrium myristoleate, yttrium palmitoleate, yttrium cis-vaccenate, yttrium paullinate, yttrium oleate, yttrium gondoate, yttrium gadoleate, lanthanum myristoleate, lanthanum palmitoleate, lanthanum cis-vaccenate, lanthanum paullinate, lanthanum oleate, lanthanum gondoate, lanthanum gadoleate, cerium myristoleate, cerium palmitoleate, cerium cis-vaccenate, cerium paullinate, cerium oleate, cerium gondoate, cerium gadoleate, praseodymium myristoleate, praseodymium palmitoleate, praseodymium cis-vaccenate, praseodymium paullinate, praseodymium oleate, praseodymium gondoate, praseodymium gadoleate, neodymium myristoleate, neodymium palmitoleate, neodymium cis-vaccenate, neodymium paullinate, neodymium oleate, neodymium gondoate, neodymium gadoleate, gadolinium myristoleate, gadolinium palmitoleate, gadolinium cis-vaccenate, gadolinium paullinate, gadolinium oleate, gadolinium gondoate, gadolinium gadoleate, dysprosium myristoleate, dysprosium palmitoleate, dysprosium cis-vaccenate, dysprosium paullinate, dysprosium oleate, dysprosium gondoate, dysprosium gadoleate, holmium myristoleate, holmium palmitoleate, holmium cis-vaccenate, holmium paullinate, holmium oleate, holmium gondoate, holmium gadoleate, erbium myristoleate, erbium palmitoleate, erbium cis-vaccenate, erbium paullinate, erbium oleate, erbium gondoate, or erbium gadoleate.

The first dispersion system may also be formed by heating a mixture of a long-chain organic acid, a hydrocarbon solvent, and one or more metal salts of one or more second organic acids; and heating that mixture to T1. T1 may be a temperature at or higher than the lower of (i) the boiling point of the second organic acid or (ii) the decomposition temperature of the second organic acid. In some embodiments, the boiling point of the second organic acid is lower than T1. T1 may comprise temperatures from 50° C. to 350° C., such as 70° C. to 200° C., or 70° C. to 150° C. Heating at T1 may last from 10 min to 100 hours, such as from 10 min to 10 hours, 10 minutes to 5 hours, 10 minutes to 3 hours, or 10 minutes to 2 hours.

The second organic acid may comprise organic acids with a molecular weight lower than the molecular weight of the long-chain organic acids such as C8-organic acids, C1 to C7, C1 to C5, or C2 to C4 organic acids. Furthermore, the second organic acid may be more volatile than the long-chain organic acids. Some examples of suitable second acids are formic acid (bp 101° C.), acetic acid (bp 118° C.), propionic acid (bp 141° C.), butyric acid (bp 164° C.), lactic acid (bp 122° C.), citric acid (310° C.), ascorbic acid (decomp 190° C.), benzoic acid (249° C.), phenol (182° C.), acetylacetone (bp 140° C.), and acetoacetic acid (decomposition 80° C. to 90° C.). The second organic acid metal salts may comprise, for example, metal acetate, metal propionate, metal butyrate, metal lactate, metal acetylacetonate, or metal acetylacetate. Without being limited by theory, the second organic acid disposed on the metal may be released from the metal by exchange with the long-chain organic acid and the second organic acid may be removed under decreased pressure or flow of inert gas. The greater volatility of the second organic acid may allow for efficient exchange as the second organic acid is removed from solution. Removal of the second organic acid may also allow for formation of the first dispersion system in a single reaction vessel and may further allow for direct use in nanoparticle formation in the same reaction vessel.

In some embodiments, the long-chain organic solvent and the long-chain organic acid are mixed prior to addition of metals, sulfur, organosulfur, or organophosphorus forming a liquid pre-mixture. To the liquid pre-mixture may be added one or more metal salts of one or more second organic acids, and optionally elemental sulfur, organosulfur, organophosphorus, or combinations thereof.

The optional sulfur or organic sulfur compounds may comprise elemental sulfur, alkyl thiols, aromatic thiols, dialkyl thioethers, diaryl thioether, alkyl disulfides, aryldisulfides, or mixture(s) thereof, such as 1-dodecanethiol (bp 266° C. to 283° C.), 1-tridecanethiol (bp 291° C.), 1-tetradecanethiol (bp 310° C.), 1-pentadecanethiol (bp 325° C.), 1-hexadecanethiol (bp 343° C. to 352° C.), 1-heptadecanethiol (bp 348° C.), 1-octadecanethiol (bp 355° C. to 362° C.), 1-icosanethiol (mp bp 383° C.), 1-docosanethiol (bp 404° C.), 1-tetracosanethiol (bp 423° C.), decyl sulfide (bp 217° C. to 218° C.), dodecyl sulfide (bp 260° C. to 263° C.), thiophenol (bp 169° C.), diphenyl sulfide (bp 296° C.), diphenyl disulfide (bp 310° C.), or mixture(s) thereof. The sulfur or organic sulfur compounds may be soluble in the long-chain organic solvent. The amount of sulfur or organic sulfur included in the first dispersion system is set by the mole ratio to the metal(s) in the first dispersion system.

The optional organophosphorus compounds may comprise alkylphosphines, dialkyl phosphines, trialkylphosphines, alkylphosphineoxides, dialkyphosphineoxides, trialkylphosphineoxides, tetraalkylphosphonium salts, and mixtures thereof. For example, suitable organophosphorus compounds may include: tributylphosphine (bp 240° C.), tripentylphosphine (bp 310° C.), trihexylphosphine (bp 352° C.), diphneylphsophine (bp 280° C.), trioctylphosphine (bp 284° C. to 291° C.), triphenylphosphine (bp 377° C.), or mixture(s) thereof. The organic phosphorus compounds may be soluble in the long-chain organic solvent. The amount of organic phosphorus included in the first dispersion system is set by the mole ratio to the metal(s) in the first dispersion system.

The first dispersion system may be substantially free of surfactants other than salts of the long-chain organic acid.

The processes of producing nanoparticle compositions of this disclosure may comprise heating the first dispersion system to a second temperature (T2), where T2 is greater than T1 and no higher than the boiling point of the long-chain hydrocarbon solvent. T2 can promote at least a portion of the first dispersion system to decompose and form a second dispersion system comprising nanoparticles described in this disclosure dispersed in the long-chain hydrocarbon solvent.

The second temperature may comprise temperatures from T2a to T2b, where T2a and T2b can be, independently, e.g., 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450° C., as long as T2a<T2b. In some embodiments, T2a is 210° C. or greater, such as where T2a=210 and T1b=450; or where T1a=250 and T1b=350.

The M1 metal salt(s), M2 metal salt(s) (if any), and M3 metal salt(s) (if any) can decompose at the second temperature to form the kernels. The kernels may be solid particles comprising the metal and oxygen atoms. The long-chain organic acids or a portion thereof may partly remain attached to the kernel's surface. Without being limited by theory, oxygen atoms from the long-chain organic acids, may be included in the kernel as a portion of the surface oxygen atoms. Such partial attachments may be sufficient to withstand washing, centrifuging, and handling of the nanoparticles. Therefore, the nanoparticle composition may comprise kernels with long-chain hydrocarbyls attached to the surface of the kernels. Without being limited by theory, the long-chain hydrocarbyls attached to the kernel may allow for uniform dispersion in the second dispersion system and complete colloidal dissolution in hydrophobic solvents.

Furthermore, some portion of the long-chain organic acid salt may decompose to form an unsaturated compound (e.g. long-chain olefins) becoming a portion of the second dispersion system. The unsaturated compound may be identical to the long-chain hydrocarbon solvent if the solvent chosen is an alpha-olefin one carbon length shorter than the long-chain organic acid.

The decomposition of the metal salts forms kernels where two or three dimensions are from 4 nm to 100 nm in length, such as from 4 nm to 20 nm in length. The kernels can have a size distribution of 30% or less, 20% or less, 10% or less, or 5% or less, such as from 1% to 30%, from 5% to 20%, or from 5% to 10%. The size and size distribution are determined by TEM and SAXS.

The processes may take place in one or more reaction vessels under an inert atmosphere. The processes may comprise separating the nanoparticle composition from the long-chain hydrocarbon solvent. A suitable method of separating the nanoparticles from the long-chain hydrocarbon solvent may comprise addition of a counter-solvent causing precipitation of the nanoparticles. Suitable counter solvents may include: C1-C8 alcohols, such as C1-$C_6$, C2-C4, or 1-butanol. Without being limited by theory, the increased polarity of the solution may cause the nanoparticles to precipitate out of solution where the counter solvent dissolves in the long-chain hydrocarbon solvent and long-chain organic acid mixture. Contaminants including unreacted metal salts, organic acids and corresponding salts may remain in the mixture of long-chain hydrocarbon solvent and counter-solvent and be removed in the process. The mixture of solvents and contaminants may be removed by centrifugation and decantation or filtration.

The processes may also include further purification of the nanoparticles by a cleaning process. The cleaning may comprise (i) dispersing the nanoparticles in a hydrophobic solvent such as benzene, pentane, toluene, hexanes, or xylenes; (ii) adding a counter solvent to precipitate the nanoparticles; and (iii) collecting the precipitate by centrifugation or filtration. Cleaning, comprising steps (i) through (iii), may be repeated to further purify the nanoparticles.

Nanoparticle Support

Purified and/or unpurified nanoparticles may be dispersed in liquid media to form a nanoparticle dispersion. Suitable liquid media for forming a nanoparticle dispersion may include: benzene, pentane, toluene, hexanes, or xylenes. The nanoparticles may also be dispersed on a solid support by contacting the nanoparticle dispersion with the support.

Suitable methods for contacting the nanoparticle dispersion with a solid support include: wet deposition, wet impregnation, or incipient wetness impregnation of the solid support. If the support is a large (greater than 100 nm) flat surface the nanoparticles may self-assemble into a monolayer on the support.

The supported nanoparticle composition of this disclosure comprises a support material (which may be called a carrier or a binder). The support material may be included at any suitable quantity, e.g., ≥20, ≥30, ≥40, ≥50, ≥60, ≥70, ≥80, ≥90, or even ≥95 wt %, based on the total weight of the supported nanoparticle composition. In supported nanoparticle compositions, the nanoparticle component can be suitably disposed on the internal or external surfaces of the support material. Support materials may comprise porous materials that provide mechanical strength and a high surface area. Non-limiting examples of suitable support materials can include: oxides (e.g. silica, alumina, titania, zirconia, or mixture(s) thereof), treated oxides (e.g. sulfated), crystalline microporous materials (e.g. zeolites), non-crystalline microporous materials, cationic clays or anionic clays (e.g. saponite, bentonite, kaoline, sepiolite, or hydrotalcite), carbonaceous materials, or combination(s) and mixture(s) thereof. A support material can be sometimes called a binder in a supported nanoparticle composition.

The supported nanoparticle composition of this disclosure may optionally comprise a solid diluent material. A solid diluent material is a solid material used to decrease nanoparticle to solid ratio and may be a material selected from conventional support materials. For example, a solid diluent material may be oxides (e.g. silica, alumina, titania, zirconia, or mixture(s) thereof), treated oxides (e.g. sulfated), crystalline microporous materials (e.g. zeolites), non-crystalline microporous materials, cationic clays or anionic clays (e.g. saponite, bentonite, kaoline, sepiolite, or hydrotalcite), carbonaceous materials, or combination(s) and mixture(s) thereof.

The nanoparticles can be combined with a support material, an optional promoter, or an optional solid diluent material, to form a supported nanoparticle composition. The combination of the support material and the nanoparticles can be processed in any suitable forming processes, including but not limited to: grinding, milling, sifting, washing, drying, calcination, and the like. Drying or calcining the nanoparticles, optional promoter, and optional solid diluent material, on a support produces a catalyst composition. Drying and Calcining may take place at a third temperature (T3). The third temperature may comprise temperatures from T3a to T3b, where T3a and T3b can be, independently, e.g., 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650° C., as long as T2a<T2b. In some embodiments, T2a is 500° C. or greater, such as where T2a=500° C. and T1b=650° C.; or where T1a=550° C. and T1b=600° C. The catalyst composition may be then disposed in a conversion reactor to perform its intended function, such as a syngas converting reactor in a syngas converting process.

It is also contemplated that the nanoparticles may be combined or formed with a precursor of a support material to obtain a catalyst composition precursor mixture. Suitable precursors of various support materials can include, e.g., alkali metal aluminates, water glass, a mixture of alkali metal aluminates and water glass, a mixture of sources of a di-, tri-, and/or tetravalent metal, such as a mixture of water-soluble salts of magnesium, aluminum, and/or silicon, chlorohydrol, aluminum sulfate, or mixture(s) thereof. The catalyst composition precursor mixture comprising the support and nanoparticles is subsequently subject to drying and calcining, resulting in the formation of the catalyst composition and the support material substantially in the same step.

A promoter may be added to a supported nanoparticle composition or a catalyst composition forming a catalyst precursor composition. The catalyst precursor may be dried and/or calcined to form a catalyst composition comprising a promoter. Promoters may include sulfur, phosphorus, or salts of elements selected from Groups 1, 7, 11, or 12 of the periodic table, such as Li, Na, K, Rb, Cs, Re, Cu, Zn, Ag, and mixture(s) thereof. Typically, sulfide and sulfate salts are used. For example, a promoter may be added to a supported nanoparticle composition or a catalyst composition as part of a solution, the solvent can then be removed via evaporation (e.g. an aqueous solution where the water is later removed).

Without being bound by a particular theory, it is believed that the metal oxide(s), and possibly the elemental phases of M1 in the kernel provide the catalytic activity for chemical conversion processes such as a Fischer-Tropsch synthesis. One or more of M2 and/or M3 can provide direct catalytic function as well. In addition, one or more of M2 and/or M3 can perform the function of a "promoter" in the supported nanoparticle composition. Furthermore, sulfur and or phosphorus, if present, can perform the function of a promoter in the catalyst composition as well. Promoters typically improve one or more performance properties of a catalyst. Example properties of catalytic performance enhanced by inclusion of a promoter in a catalyst over the catalyst composition without a promoter, may include: selectivity, activity, stability, lifetime, regenerability, reducibility, and resistance to potential poisoning by impurities such as sulfur, nitrogen, and oxygen.

It may be advantageous for the nanoparticles to be uniformly dispersed on the support. The nanoparticles can be substantially homogeneously distributed in the supported nanoparticle composition, resulting in a highly dispersed distribution, which can contribute to a high catalytic activity of a catalyst composition.

The synthesis methods disclosed may produce crystalline kernels with uniform particle shape and size. The kernels comprise metal oxide(s) that may be uniformly distributed throughout the kernel, which may improve catalysis when the kernel is included in a catalyst composition. The kernel may be part of a nanoparticle which may comprise long-chain hydrocarbons disposed on the kernel. The nanoparticles may be formed in a single reaction vessel from readily available precursors. The nanoparticle may be dispersed in liquid media, and thereby dispersed on a solid support. The nanoparticles dispersed on solid support may together be dried and or calcined to form a catalyst composition Processes for Converting Syngas The supported nanoparticle composition and/or the catalyst composition of this disclosure may be used in any process where the relevant metal(s) and/or the metal oxide(s) can perform a catalytic function. The supported nanoparticle composition and/or the catalyst composition of this disclosure can be particularly advantageously used in processes for converting syngas into various products such as alcohols and olefins, particularly C1-05 alcohols, such as C1-C4 alcohols, and C2-05 olefins (particularly C2-C4 olefins), such as the Fischer-Tropsch processes. The Fischer-Tropsch process is a collection of chemical reactions that converts a mixture of carbon monoxide and hydrogen into hydrocarbons and/or alcohols. The products formed are the "conversion product mixture." These reactions occur in the presence of metal catalysts, typically at temperatures of 100 to 500° C. (212 to 932° F.) and pressures of one to several tens of atmospheres.

The term "syngas" as used herein relates to a gaseous mixture consisting essentially of hydrogen ($H_2$) and carbon monoxide (CO). The syngas, which is used as a feed stream, may comprise up to 10 mol % of other components such as $CO_2$ and lower hydrocarbons (lower HC), depending on the source and the intended conversion processes. Said other components may be side-products or unconverted products obtained in the process used for producing the syngas. The syngas may contain such a low amount of molecular oxygen ($O_2$) so that the quantity of $O_2$ present does not interfere with the Fischer-Tropsch synthesis reactions and/or other conversion reactions. For example, the syngas may comprise not more than 1 mol % $O_2$, not more than 0.5 mol % $O_2$, or not more than 0.4 mol % $O_2$. The syngas may have a hydrogen ($H_2$) to carbon monoxide (CO) molar ratio of from 1:3 to 3:1. The partial pressures of $H_2$ and CO may be adjusted by introduction of inert gas to the reaction mixture.

Syngas can be formed by reacting steam and/or oxygen with a carbonaceous material, for example, natural gas, coal, biomass, or a hydrocarbon feedstock through a reforming process in a syngas reformer. The reforming process can be based on any suitable reforming process, such as Steam Methane Reforming, Auto Thermal Reforming, or Partial Oxidation, Adiabatic Pre Reforming, or Gas Heated Reforming, or a combination thereof. Example steam and oxygen reforming processes are detailed in U.S. Pat. No. 7,485,767.

The syngas formed from steam or oxygen reforming comprises hydrogen and one or more carbon oxides (CO and $CO_2$). The hydrogen to carbon oxide ratio of the syngas produced will vary depending on the reforming conditions used. The syngas reformer product(s) should contain $H_2$, CO and $CO_2$ in amounts and ratios which render the resulting syngas blend suitable for subsequent processing into either oxygenates, such as methanol/dimethyl ether or in Fischer-Tropsch synthesis.

The syngas from reforming to be used in Fischer-Tropsch synthesis may have a molar ratio of $H_2$ to CO, unrelated to the quantity of $CO_2$, of 1.9 or greater, such as from 2.0 to 2.8, or from 2.1 to 2.6. On a water-free basis, the $CO_2$ content of the syngas may be 10 mol % or less, such as 5.5 mol % or less, or from 2 mol % to 5 mol %, or from 2.5 mol % to 4.5 mol %.

It is possible to alter the ratio of components within the syngas and the absolute $CO_2$ content of the syngas by removing, and optionally recycling, some of the $CO_2$ from the syngas produced in one or more reforming processes. Several commercial technologies are available (e.g. acid gas removal towers) to recover and recycle $CO_2$ from syngas as produced in the reforming process. In at least one embodiment, $CO_2$ can be recovered from the syngas effluent from a steam reforming unit, and the recovered $CO_2$ can be recycled to a syngas reformer.

Suitable Fischer-Tropsch catalysis procedures may be found in: U.S. Pat. Nos. 7,485,767; 6,211,255; and 6,476,085; the relevant portions of their contents being incorporated by reference. The supported nanoparticle composition and/or the catalyst composition may be contained in a conversion reactor (a reactor for the conversion of syngas), such as a fixed bed reactor, a fluidized bed reactor, or any other suitable reactor. The conversion conditions may comprise contacting the catalyst composition and/or the supported nanoparticle composition with syngas, to provide a reaction mixture, at a pressure of 1 bar to 50 bar, at a temperature of 150° C. to 450° C., and/or a gas hourly space velocity of 1000 $h^{-1}$ to 10,000 $h^{-1}$ for a reaction period.

The conversion conditions may comprise a wide range of temperatures. In at least one embodiment, the reaction temperature may be from 100° C. to 450° C., such as from 150° C. to 350° C., such as from 200° C. to 300° C. For certain catalyst compositions or supported nanoparticle compositions, lower temperature ranges might be preferred, but if the composition comprises cobalt metal, higher temperatures are tolerated. For example, a catalyst composition comprising cobalt metal may be used at reaction temperatures of 250° C. or greater, such as from 250° C. to 350° C., or from 250° C. to 300° C.

The conversion conditions may comprise a wide range of reaction pressures. In at least one embodiment, the absolute reaction pressure ranges from p1 to p2 kilopascal ("kPa"), where p1 and p2 can be, independently, e.g., 100, 150, 200, 250, 300, 350, 400, 450, 500, 600, 700, 800, 900, 1000, 1500, 2000, 2500, 3000, 3500, 4000, 4500, or 5,000, as long as p1<p2.

Gas hourly space velocities used for converting the syngas to olefins and/or alcohols can vary depending upon the type of reactor that is used. In one embodiment, gas hourly space velocity of the flow of gas through the catalyst bed is from 100 $hr^{-1}$ to 50,000 $hr^{-1}$, such as from 500 $hr^{-1}$ to 25,000 $hr^{-1}$, from 1000 $hr^{-1}$ to 20,000 $hr^{-1}$, or from 100 $hr^{-1}$ to 10,000 $hr^{-1}$.

Conversion conditions may have an effect on the catalyst performance. For example, selectivity on a carbon basis is a function of the probability of chain growth. Factors affecting chain growth include reaction temperatures, the gas composition and the partial pressures of the various gases in contact with the catalyst composition or the supported nanoparticle composition. Altering these factors may lead to a high degree of flexibility in obtaining a type of product in a certain carbon range. Without being limited by theory, an increase in operating temperature shifts the selectivity to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure, the more catalyst surface that is covered by adsorbed monomers. The lower the coverage by partially hydrogenated CO monomers, the higher the probability of chain growth. Accordingly, it is probable that the two key steps leading to chain termination are desorption of the chains yielding alkenes and hydrogenation of the chains to yield alkanes.

EXAMPLES

Example 1. Preparation of $MnCoO_x$ Spherical Nanoparticles

A reaction solution was prepared by dissolving manganese (II) acetylacetonate ($Mn(CH_3COCHCOCH_2)_2$) and Cobalt (II) acetate tetrahydrate ($Co(CH_3COO)_2.4H_2O$) in a mixture of oleic acid (OLAC) and 1-octadecene. The reaction solution had a molar ratio of 4.5 mol OLAC: mol metal and a combined metal concentration of 0.164 mmol Mn/mL of 1-octadecene. The reaction solution was heated to a temperature of 130° C. under flow of nitrogen and held at 130° C. for 90 minutes. The mixture was then heated under an inert atmosphere of nitrogen at a rate of 10° C./min to reflux (320° C.). The reaction mixture was held at 320° C. for 30 min. The reaction mixture was cooled under an inert atmosphere using a flow of RT air to cool the exterior of the reaction vessel. The nanoparticles were collected and purified via repeated washing and decanting/centrifugation steps using hexane as a hydrophobic solvent, and isopropanol as a counter solvent. The purified nanoparticles were dispersed in toluene. TEM imagery shows that the nanoparticles are roughly spherical in shape, have an average diameter of 6.3 nanometers and a size distribution of 13%.

Example 1a. Supporting $MnCoO_x$ Spherical Nanoparticles with Silica

Eight grams of $SiO_2$ was dispersed in hexane. While under vigorous stirring, the nanoparticle solution prepared according to Example 1 was added to the support dispersion and the mixture was stirred at 25° C. for 180 minutes. The catalyst powder was recovered by centrifugation. The powder was washed three times with hexane via sonication and centrifugation. The supported nanoparticle composition was dried at 60° C. for 12 hours under vacuum (100 mmHg). The dried supported nanoparticle powder was then calcined in static air at 325° C. for 180 minutes using heating and cooling ramps of 3° C. per minute.

Example Lb. Supporting $MnCoO_x$ Spherical Nanoparticles with Alumina

Eight grams of $Al_2O_3$ was dispersed in hexane. While under vigorous stirring, the nanoparticle solution prepared according to Example 1 was added to the support dispersion and the mixture was stirred at 25° C. for 180 minutes. The catalyst powder was recovered by centrifugation. The powder was washed three times with hexane via sonication and centrifugation. The supported nanoparticle composition was dried at 60° C. for 12 hours under vacuum (100 mmHg). The dried supported nanoparticle powder was then calcined in static air at 325° C. for 180 minutes using heating and cooling ramps of 3° C. per minute.

Example 2. Preparation of Supported $MnCoO_x$ Rod-Shaped Nanoparticles

A reaction solution was prepared by dissolving manganese (II) acetylacetonate acetate ($Mn(CH_3COCHCOCH_2)_2$) and Cobalt (II) acetate tetrahydrate ($Co(CH_3COO)_2.4H_2O$) in a mixture of oleic acid (OLAC) and 1-octadecene. The reaction solution had a molar ratio of 4.5 mol OLAC: mol Metal (Mn+Co) and a combined metal concentration of 0.9 mmol Mn/mL of 1-octadecene. The reaction solution was heated to a temperature of 130° C. under flowing nitrogen and held at 130° C. for 60 minutes. The mixture was then heated under an inert atmosphere of nitrogen at a rate of 10° C./min to reflux (320° C.). The reaction mixture was held at 320° C. for 120 min. The reaction mixture was cooled under an inert atmosphere using a flow of RT air to cool the exterior of the reaction vessel. The nanoparticles were collected and purified via repeated washing and decanting/centrifugation steps using hexane as a hydrophobic solvent, and isopropanol as a counter solvent. The purified nanoparticles were dispersed in toluene. TEM images illustrated that the nanoparticles are rod-shaped, have an average length of 64.1 with a length distribution of 15% and an average width of 11.7 nanometers with a width distribution of 13%.

Comparative Example 3. Bulk $Co_2MnO_4$

An aqueous solution was prepared containing 48.9 g of $Co(NO_3)_2$-$6H_2O$ and 24.1 g of $Mn(NO_3)$-$2.6H_2O$ in 125 ml water. This was added to an aqueous solution of 48.4 g citric acid and 14.1 mi ethylene glycol in 25 ml water with stirring at 70° C. to 90° C. The mixture became thick after 1-2 hours, after which it was calcined in air at 350° C. for 30 minutes.

FIG. 1 shows catalyst selectivity in production C2-C4 hydrocarbons versus percent CO conversion. Bulk cobalt/manganese mixed metal oxide catalyst is shown as triangles 102 and a catalyst composition with 6.3 nm spherical cobalt/manganese mixed metal oxide nanoparticles according to example 1a are shown as circles 104. The comparison of the bulk and silica supported nanoparticle catalyst compositions shows that at higher conversion rates the selectivity towards C2 to C4 hydrocarbons is similar between 102 and 104.

Figure 2:
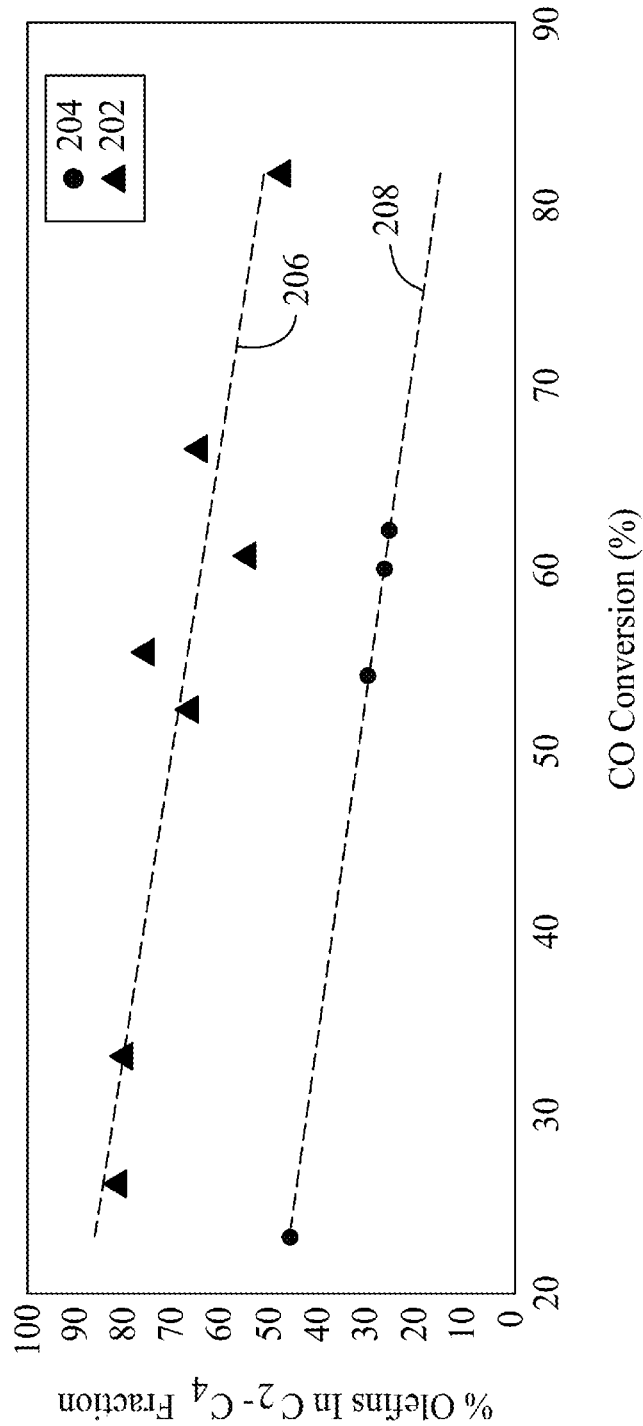
FIG. 2 is a graph showing the percent of olefins in the C2-C4 fraction versus CO conversion rate in syngas conversion, according to an embodiment.

FIG. 2 shows the percent of olefins contained in the C2-C4 hydrocarbons produced versus percent CO conversion. Bulk cobalt/manganese mixed metal oxide catalyst is shown as triangles 202 and a catalyst composition with 6.3 nm spherical cobalt/manganese mixed metal oxide nanoparticles according to example 1a are shown as circles 204. The comparison of the bulk and silica supported nanoparticle catalyst compositions shows that the catalyst composition comprising silica supported nanoparticles has a greater percentage of olefins in the C2-C4 hydrocarbons produced at all conversion rates over the bulk mixed metal oxide catalyst. Both the bulk and nanoparticle catalysts demonstrate a downward trend of less olefin in the C2-C4 hydrocarbon as conversion increases. The downward trend line 206 is a linear regression of triangles 202 for the supported nanoparticle catalyst composition, and the downward trend line 208 is a linear regression of circles 204 for the bulk mixed metal oxide catalyst composition.

Figure 3:
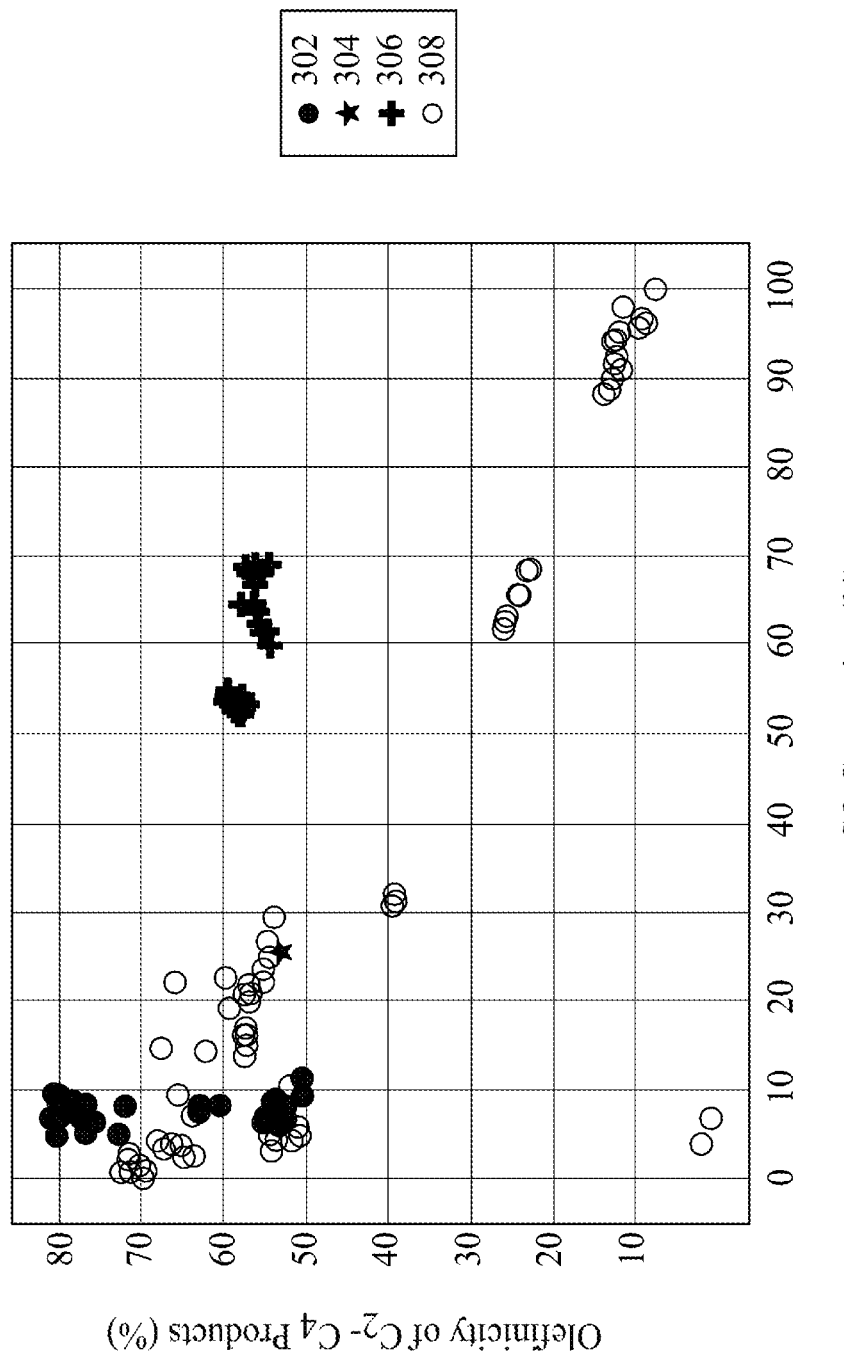
FIG. 3 is a graph showing the olefinicity in the C2-C4 fraction versus CO conversion rate in syngas conversion, according to an embodiment.

FIG. 3 shows the olefinicity of the C2-C4 hydrocarbons produced versus percent CO conversion. A catalyst composition with 6.3 nm spherical cobalt/manganese mixed metal oxide nanoparticles according to example 1b were used at three temperature in Fischer-Tropsch synthesis: (i) the use of alumina supported nanoparticles at 250° C. is shown as dots 302; (ii) the use of alumina supported nanoparticles at 270° C. is shown as stars 304; and (i) the use of alumina supported nanoparticles at 290° C. is shown as crosses 306. Bulk cobalt/manganese mixed metal oxide catalyst is shown as rings 308. The comparison of the bulk catalyst composition and the alumina supported nanoparticle catalyst composition shows that the catalyst composition comprising alumina supported nanoparticles has a greater percentage of olefins in the C2-C4 hydrocarbons produced at various conversion rates and temperatures over the bulk mixed metal oxide catalyst. Both the bulk and nanoparticle catalysts demonstrate a downward trend of less olefin in the C2-C4 hydrocarbon as conversion increases.

Figure 4:
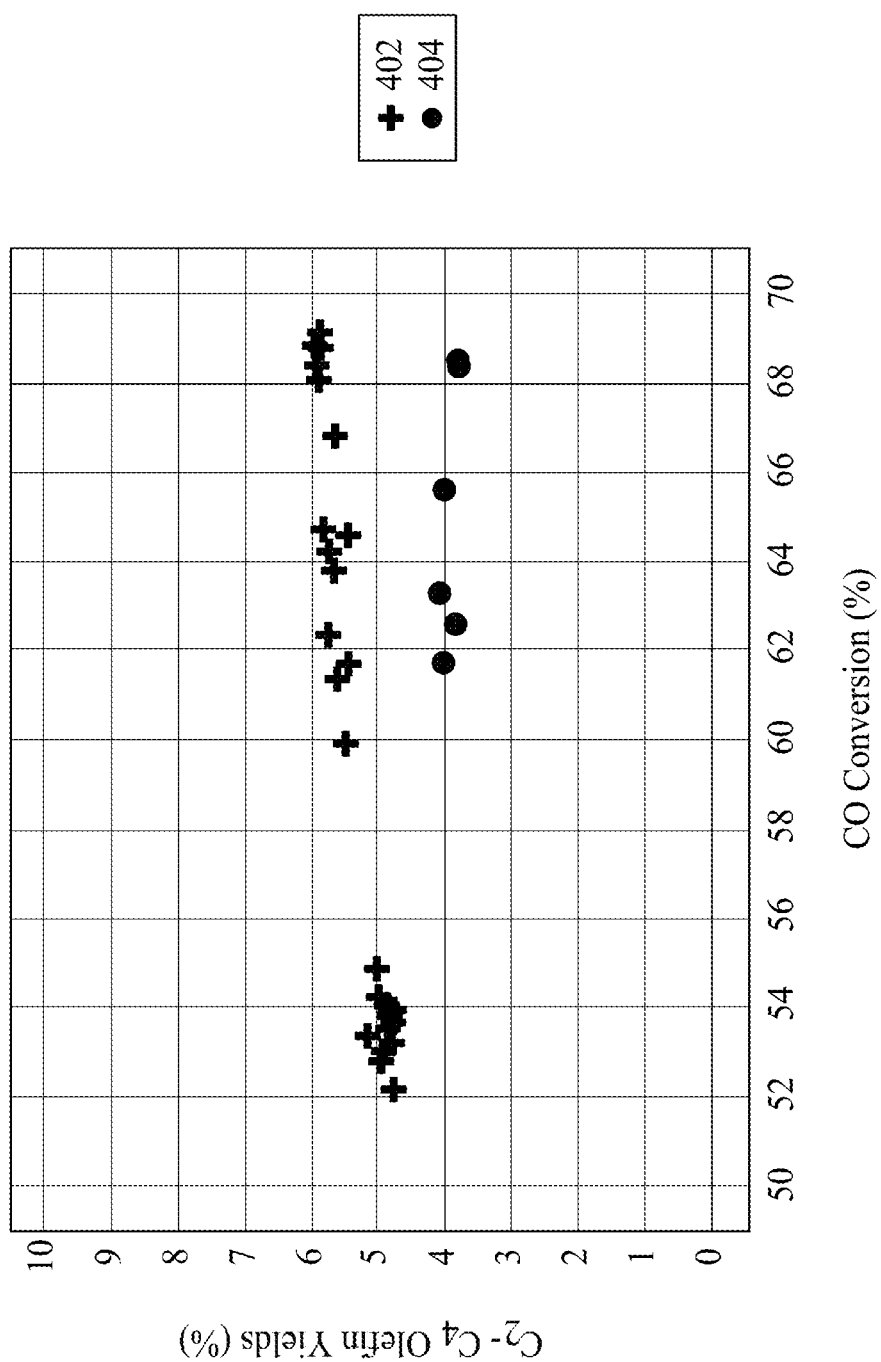
FIG. 4 is a graph showing the C2-C4 olefin yield versus CO conversion rate in syngas conversion, according to an embodiment.

FIG. 4 shows the yield of olefins C2-C4 hydrocarbons produced versus percent CO conversion. Yield was calculated by multiplying the conversion and the selectivity. A catalyst composition with 6.3 nm spherical cobalt/manganese mixed metal oxide nanoparticles according to example 1b are shown as crosses 402 and bulk cobalt/manganese mixed metal oxide catalyst is shown as dots 404. The comparison of the olefin yield of the bulk catalyst composition and the alumina supported nanoparticle catalyst composition shows that the catalyst composition comprising alumina supported nanoparticles has a greater yield of C2-C4 olefins at all conversion rates over the bulk mixed metal oxide catalyst.

Other non-limiting aspects and/or embodiments of the present disclosure can include:

A1. A supported nanoparticle composition comprising:
a support; and
a plurality of nanoparticles on the support, where:
each nanoparticle comprises a kernel, the kernels have an average particle size from 4 to 100 nm and a particle size distribution, expressed as a percentage of the standard deviation of the particle size relative to the average particle size, of no greater than 20%, as determined by small angle X-ray scattering ("SAXS") and transmission electron microscopy ("TEM") image analysis; the kernels comprise oxygen, a metal element M1, optionally sulfur, optionally phosphorus, optionally a metal element M2, and optionally a third metal element M3, where M1 is selected from Mn, Fe, Co, and combination of two or more thereof in any proportion, M2 is selected from Ni, Zn, Cu, Mo, W, Ag, and combinations thereof, and M3 is selected from Y, Sc, alkaline metals, the lanthanides, group 13, 14, and 15 elements, and combinations thereof, and the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$.

A2. The supported nanoparticle composition of A1, where $0 \leq r1 \leq 0.5$, and $0 \leq r2 \leq 0.5$.

A3. The supported nanoparticle composition of A2, where $0.05 \leq r1 \leq 0.5$, and $0.005 \leq r2 \leq 0.5$.

A4. The supported nanoparticle composition of any of A1 to A3, where the kernels comprise a crystalline phase of an oxide of the at least one metal element selected from M1, M2, and M3.

A5. The supported nanoparticle composition of any of A1 to A4, where the nanoparticles have an average particle size from 4 to 35 nm.

A6. The supported nanoparticle composition of any of A1 to A5, where the nanoparticles have a size distribution of from 5 to 15%.

A7. The supported nanoparticle composition of any of A1 to A6, where the kernels comprise at least two metal elements.

A8. The supported nanoparticle composition of A7, where the at least two metal elements are uniformly distributed in the nanoparticles.

A9. The supported nanoparticle composition of any of embodiments A1 to A8, where the nanoparticles comprise a plurality of hydrophobic long-chain groups attached to the surface of the kernels.

A10. The supported nanoparticle composition of A7, where the long-chain groups comprise a C14-C24 hydrocarbyl group.

A11. The supported nanoparticle composition of any of A1 to A10, where the nanoparticles consist essentially of oxygen, M1, optionally M2, optionally M3, optionally sulfur, and optionally phosphorus.

A12. The supported nanoparticle composition of A11, where the nanoparticles are substantially free of long-chain groups attached to the surface of the kernels.

A13. The supported nanoparticle composition of A11 or A12, where the kernels consist essentially of oxygen, M1, optionally M2, optionally M3, optionally sulfur, and optionally phosphorus.

A14. The supported nanoparticle composition of A13, where the kernels consist essentially of a promoter and a mixed oxide selected from Fe and Mn; Co and Mn; or Fe, Cu, and Zn.

A15. The supported nanoparticle composition of any of A1 to A14, where the kernels are substantially spherical.

A16. The supported nanoparticle composition of any of A1 to A15, where the kernels are rod-shaped.

A17. The supported nanoparticle composition of A16, where the kernels have an aspect ratio of >1 to 10.

B1. A process for making the composition of any of A1 to A12, comprising:
(I) providing a nanoparticle dispersion comprising a liquid medium and a plurality of nanoparticles distributed therein, where each nanoparticle comprises a kernel, the kernels have an average particle size from 4 to 100 nm and a particle size distribution, expressed as a percentage of the standard deviation of the particle size relative to the average particle size, of no greater than 20%, as determined by small angle X-ray scattering ("SAXS") and transmission electron microscopy ("TEM") image analysis; the kernels comprise oxygen, a metal element M1, optionally sulfur, optionally phosphorus, optionally a second metal element M2, and optionally a third metal element M3, where M1 is selected from Mn, Fe, Co, and combination of two or more thereof in any proportion, M2 is selected from Ni, Zn, Cu, Mo, W, Ag, and combinations thereof, and M3 is selected from Y, Sc, alkaline metals, the lanthanides, group 13, 14, and 15 elements, and combinations thereof, and the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$; and (II) disposing a quantity of the nanoparticle dispersion on a support to obtain a supported nanoparticle composition.

B2. The process of B1, further comprising:
(III) removing at least a portion of the liquid medium from the supported nanoparticle composition.

B3. The process of B1 or B2, further comprising:
(IV) calcining the supported nanoparticle composition to obtain a catalyst composition.

B3. The process of any of B1 to B3, further comprising:
(V) impregnating the support, the supported nanoparticle composition, or catalyst composition with a precursor of an promoter to obtain a catalyst precursor; and
(VI) drying and/or calcining the catalyst precursor to obtain a catalyst composition comprising a promoter.

B4. The process of B1 to B4, where step (I) comprises:
(Ia) providing a first dispersion system at a first temperature, the first dispersion system comprising a salt of a long-chain organic acid and M1, optionally a salt of the long-chain organic acid and M2, optionally a salt of the long-chain organic acid and M3, a long-chain hydrocarbon solvent, optionally a salt of a second organic acid and M1, optionally a salt of a third organic acid and M2, optionally a salt of a fourth organic acid and M3, optionally sulfur or an organic sulfur compound soluble in the long-chain hydrocarbon solvent, and optionally an organic phosphorous compound soluble in the long-chain hydrocarbon solvent; and
(Ib) heating the first dispersion system to a second temperature higher than the first temperature but no higher than the boiling point of the long-chain hydrocarbon solvent, where at least a portion of the salt(s) of the long-chain organic acid and at least a portion of the salt(s) of the second organic acid, if present, decompose to form a second dispersion system comprising nanoparticles dispersed in the long-chain hydrocarbon solvent, and the nanoparticles comprise kernels, and the kernels comprise M1, optionally M2, optionally M3, oxygen, optionally sulfur, and optionally phosphorus;

(Ic) separating the nanoparticles from the second dispersion system; and (Id) dispersing the nanoparticles separated in (Ic) in the liquid medium to form the nanoparticle dispersion.

B5. The process of any of B1 to B4, where the nanoparticles further comprise long hydrocarbon chains attached to the surface of the kernels.

B6. The process of any of B1 to B5, where the nanoparticles have an average particle size in a range from 4 to 100 nm, and a particle size distribution of no greater than 20%, expressed as the percentage of the standard deviation of the particle size relative to the average particle size, as determined by small angle X-ray scattering ("SAXS") and transmission electron microscopy ("TEM") image analysis.

B7. The process of B6, where the nanoparticles have an average particle size in a range from 4 to 20 nm, as determined by SAXS and TEM image analysis.

B8. The process of any of B4 to B7, where step (Ia) comprises:
(Ia.1) providing a first liquid mixture of the long-chain organic acid, the long-chain hydrocarbon solvent, and the salt of the second organic acid and M1, the optional salt of the third organic acid and M2, and the optional salt of the fourth organic acid and M3;
(Ia.2) heating the second mixture to the first temperature to obtain the first dispersion system.

B9. The process of B8, where steps (Ia.1), (Ia.2), and (Ib) are all performed in the same vessel.

B10. The process of B8 or B9, where in step (Ia.1), the first liquid mixture comprises (i) elemental sulfur and/or an organic-sulfur compound soluble in the long-chain hydrocarbon solvent, and/or (ii) a phosphorous-containing organic compound soluble in the long-chain hydrocarbon solvent at the first temperature.

B11. The process of any of B8 to B10, where step (Ia.1) comprises:
(Ia. 1a) mixing the long-chain organic acid with the long-chain hydrocarbon solvent to obtain a liquid pre-mixture;
(Ia. 1b) adding, to the liquid pre-mixture obtained in (Ia. 1a), (i) the salt of the second organic acid and M1, optionally the salt of the third organic acid and M2, and optionally the salt of the fourth organic acid and M3; (ii) optionally elemental sulfur and/or an organic-sulfur compound soluble in the long-chain hydrocarbon solvent, and (iii) optionally a phosphorous-containing organic compound soluble in the long-chain hydrocarbon solvent at the first temperature.

B12. The process of any of B4 to B11, where the first dispersion system is substantially free of a surfactant other than the salt(s) of the long-chain organic acid.

B13. The process of embodiment B5, where in step (Ia.2), the first mixture is heated to a temperature no lower than the boiling points of the second organic acid, the third organic acid if the salt of the third organic acid and M2 is added to the first mixture, the fourth organic acid if the salt of the fourth organic acid and M3 is added to the first mixture, or the decomposition temperatures of the second organic acid, the third organic acid, and the fourth organic acid, whichever is lower.

B14. The process of any of B11 to B13, where the second organic acid has a boiling point lower than the first temperature.

B15. The process of embodiment B6, where the second organic acid is selected from: formic acid, acetic acid, citric acid, propionate acid, actylacetonic acid, ascorbic acid, benzylic acid, phenol, acetoacetone, and the like.

B16. The process of embodiment B15, where the second organic acid is acetic acid.

B17. The process of any of embodiments B11 to B16, where the second mixture is heated to a temperature in a range from 70° C. to 150° C.

B18. The process of embodiment B17, where the second mixture is heated to a temperature in a range from 70° C. to 200° C. for a period of t minutes, where $10 \leq t \leq 120$.

B18. The process of any of B4 to B18, where the second temperature is at least 210° C.

B19. The process of any of embodiments B4 to B18, where the second temperature is in a range from 210° C. to 450° C.

B20. The process of any of embodiments B4 to B19, where the long-chain organic acid is selected from C14-C24 fatty acids and mixtures of two or more thereof, and the long-chain hydrocarbon solvent is selected from a C14-C24 hydrocarbons and mixtures of two or more thereof.

B21. The process of embodiment B20, where the long-chain organic acid is selected from C14-C24 monounsaturated fatty acids, and mixtures of two or more thereof, and/or the long-chain hydrocarbon solvent is selected from a C14-C24 unsaturated hydrocarbons and mixtures of two or more thereof.

B22. The process of embodiments B20 or B21, where the long-chain organic acid and the long-chain hydrocarbon solvent do not differ in number of average carbon atoms per molecule by more than 4.

B23. The process of any of embodiments B4 to B22, where the long-chain organic acid is oleic acid, and the long-chain hydrocarbon solvent is 1-octadecene.

B24. The process of any of embodiments B4 to B23, where step (I) and/or step (II) are performed in the presence of an inert atmosphere.

B25. The process of any of embodiments B4 to B24 wherein in step (Ia) M1, M2, M3, and M4 are present in the long-chain hydrocarbon solvent at a concentration of $\geq 0.5$ mmol/mL.

C1. A process for converting syngas, the process comprising contacting a feed comprising syngas with a composition of any of A1 to A16 in a conversion reactor under conversion conditions to produce a conversion product mixture.

C2. The process of C1, where the conversion product mixture comprises one more of a C1-05 alcohol and/or one or more of a C2-05 olefin.

C3. The process of C1 or C2, where the nanoparticles in the supported nanoparticle composition consist essentially of oxygen, M1, optionally M2, optionally M3, optionally sulfur, and optionally phosphorus.

C4. The process of C3, where the nanoparticles are substantially free of long-chain groups attached to the surface of the kernels.

C5. The process of C3 or C4, where the nanoparticles in the composition consist essentially of oxygen, M1, optionally M2, optionally M3, optionally sulfur, and optionally phosphorus.

C6. The process of C5, where the nanoparticles consist essentially of a promoter and a mixed oxide selected from Fe and Mn; Co and Mn; or Fe, Cu, and Zn.

C7. The process of any of C1 to C6, where the conversion conditions comprise a temperature of from 150° C. to 350° C., an absolute pressure of from 1 bar to 50 bar, a $H_2$:CO ratio of from 1:3 to 3:1, and a GHSV of from 1,000 $h^{-1}$ to 10,000 $h^{-1}$.

D1. A composition comprising a metal oxide represented by Formula (F-1):

$$M_aM'_bO_x \quad (F\text{-}1)$$

where:
M is a first metal selected from manganese, iron, cobalt, or a combination thereof;
M' is a second metal selected from transition metals and main group elements other than the first metal;
a and x are independently greater than 0 to 1; and
b is from 0 to 1;
where:
the metal oxide has a particle size of from about 4 nm to about 35 nm; and
the metal oxide has a size distribution having a standard deviation of about 20% or less based on the particle size.

D2. The composition of embodiment D1, where the first metal is manganese.

D3. The composition of any of embodiments D1 to D2, where the second metal is selected from zinc, copper, or tin.

D4. The composition of any of embodiments D1 to D3, where the ratio of a:b is from about 1:3 to about 2:1.

D5. The composition of any of embodiments D1 to D4, where one or more long-chain organic acids are disposed on the metal oxide.

D6. The composition of embodiment D5, where the one or more long-chain organic acids is oleic acid.

E1. A process of producing a composition comprising:
a metal oxide represented by Formula (F-1):

$$M_aM'_bO_x \quad (F\text{-}1)$$

where:
M is a first metal selected from manganese, iron, cobalt, or a combination thereof;
M' is a second metal selected from transition metals, and main group elements other than the first metal;
a and x are independently greater than 0 to 1; and
b is from 0 to 1;
where:
the metal oxide has a particle size of from about 4 nm to about 20 nm; and
the metal oxide has a size distribution having a standard deviation of about 20% or less based on the particle size,
the process comprising:
introducing at least one organic metal salt, a long-chain organic acid, and a non-coordinating solvent to a reaction vessel to form a reaction mixture, where the non-coordinating solvent has a boiling point of about 200° C. or higher; and
applying heat to the first reaction mixture to form a product mixture.

E2. The process of embodiment E1, further comprising heating the reaction mixture from about 70° C. to about 150° C. for from about 30 minutes to about 3 hours in an inert atmosphere.

E3. The process of embodiment E1, further comprising heating the reaction mixture from about 70° C. to about 150° C. for from about 30 minutes to about 3 hours under pressure reduced below atmospheric pressure.

E4. The process of any of embodiments E1 to E3, further comprising cooling the product mixture to form a cooled product mixture.

E5. The process of embodiment E4, further comprising precipitating the cooled product mixture with a polar solvent selected from ethanol or isopropanol to form a precipitated composition.

E6. The process of embodiment E5, further comprising:
centrifuging the precipitated composition to form a supernatant and a pellet; and
decanting the supernatant.

E7. The process of embodiment E6, further comprising washing the pellet, where washing comprises:
dissolving the pellet in a non-polar solvent to form a solution;
precipitating a purified precipitated composition from the solution using a polar solvent;
centrifuging the purified precipitated composition to form a supernatant; and
decanting the supernatant.

E8. The process of any of embodiments E1 to E7, where the at least one organic metal salt comprises a mixture of organic salts of the first metal and the second metal.

E9. The process of embodiment E8, where the ratio a:b is from about 1:3 to about 2:1.

E10. The process of any of embodiments E1 to E9, where a molar ratio of metal salt to long-chain organic acid of the reaction mixture is from about 1:2 to about 1:8.

E11. The process of any of embodiments E1 to E10, where the non-coordinating solvent is selected from C14+ straight-chain alkanes or alkenes.

E12. The process of any of embodiments E1 to E11, where the non-coordinating solvent is 1-octadecene.

E13. The process of any of embodiments E1 to E12, where the long-chain organic acid is oleic acid.

E14. The process of any of embodiments E1 to E13, where the reaction time period is from about 5 minutes to about 3 hours.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this disclosure. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A supported nanoparticle composition comprising:
   a support; and
   a plurality of nanoparticles on the support, wherein:
   each nanoparticle comprises a kernel, the kernels have an average particle size from 4 to 100 nm and a particle size distribution of no greater than 20%, the kernels are substantially spherical or rod-shaped, the kernels comprise oxygen, a metal element M1, optionally sulfur, optionally phosphorus, an optional metal element M2, and optionally a third metal element M3, where:
   M1 is selected from Mn, Fe, Co, and combination of two or more thereof;
   M2 is selected from Ni, Zn, Cu, Mo, W, Ag, and combinations thereof;
   M3 is selected from Al, Ga, In, Th, Y, Sc, the lanthanide series, and combinations thereof; and
   the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$.

2. The supported nanoparticle composition of claim 1, wherein $0.05 \leq r1 \leq 0.5$, and $0.005 \leq r2 \leq 0.5$.

3. The supported nanoparticle composition of claim 1, wherein the kernels comprise an oxide of at least one metal element from the M1, the M2, or the M3.

4. The supported nanoparticle composition of claim 1, wherein the nanoparticles have an average particle size of from 4 to 20 nm.

5. The supported nanoparticle composition of claim 1, wherein the nanoparticles have a particle size distribution of from 5 to 15%.

6. The supported nanoparticle composition of claim 1, wherein the kernels comprise at least two metal elements.

7. The supported nanoparticle composition of claim 1, wherein the nanoparticles are substantially free of long-chain groups attached to the surface of the kernels.

8. The supported nanoparticle composition of claim 1, wherein the kernels consist essentially of oxygen, M1, optionally M2, optionally M3, optionally sulfur, and optionally phosphorus.

9. A process for converting syngas, the process comprising contacting a feed comprising syngas with a composition of claim 1 in a conversion reactor under conversion conditions to produce a conversion product mixture.

10. The process of claim 9, wherein the conversion product mixture comprises one or more of a C1-C5 alcohol and/or one or more of a C2-C5 olefin.

11. The process of claim 9, wherein the nanoparticles are substantially free of long-chain groups attached to the surface of the kernels.

12. The process of claim 9, wherein the nanoparticles consist essentially of a promoter and a mixed oxide of Fe and Mn; Co and Mn; or Fe, Cu, and Zn.

13. The process of claim 9, wherein the conversion conditions comprise a temperature of from 150° C. to 350° C., an absolute pressure of from 1 bar to 50 bar, a $H_2$:CO ratio of from 1:3 to 3:1, and a GHSV of from 1,000 $h^{-1}$ to 10,000 $h^{-1}$.

14. The process of claim 1, wherein M3 is Al, Ga, In, Th, and combinations thereof.

15. A process for making a supported nanoparticle composition, comprising:
   (I) providing a nanoparticle dispersion comprising a liquid medium and a plurality of nanoparticles distributed therein, wherein each nanoparticle comprises a kernel, the kernels have an average particle size from 4 to 100 nm and a particle size distribution of 20% or less; the kernels comprise oxygen, a metal element M1, optionally sulfur, optionally phosphorus, optionally a second metal element M2, and optionally a third metal element M3, where:
   M1 is selected from Mn, Fe, Co, or a combination of two or more thereof;
   M2 is selected from Ni, Zn, Cu, Mo, W, Ag, and combinations thereof;
   M3 is selected from Y, Sc, alkaline metals, the lanthanides, group 13, 14, and 15 elements, and combinations thereof; and
   the molar ratios of M2, M3, S, and P, if any, to M1 is r1, r2, r3, and r4, respectively, $0 \leq r1 \leq 2$, $0 \leq r2 \leq 2$, $0 \leq r3 \leq 5$, and $0 \leq r4 \leq 5$; and
   (II) disposing a quantity of the nanoparticle dispersion on a support to obtain a supported nanoparticle composition.

16. The process of claim 15, further comprising:
   (IV) calcining the supported nanoparticle composition to obtain a catalyst composition.

17. The process of claim 15, further comprising:
   (V) impregnating the support or the supported nanoparticle composition with a precursor of an promoter to obtain a catalyst precursor; and
   (VI) drying and/or calcining the catalyst precursor to obtain a catalyst composition comprising a promoter.

18. The process of any of claim 15, wherein step (I) comprises:
   (Ia) providing a first dispersion system at a first temperature, the first dispersion system comprising a salt of a long-chain organic acid and M1, optionally a salt of the long-chain organic acid and M2, optionally a salt of the long-chain organic acid and M3, a long-chain hydrocarbon solvent, optionally a salt of a second organic acid and M1, optionally a salt of a third organic acid and M2, optionally a salt of a fourth organic acid and M3, optionally sulfur or an organic sulfur compound soluble in the long-chain hydrocarbon solvent, and optionally an organic phosphorous compound soluble in the long-chain hydrocarbon solvent; and
   (Ib) heating the first dispersion system to a second temperature higher than the first temperature but no higher than the boiling point of the long-chain hydrocarbon solvent, where at least a portion of the salt(s) of the long-chain organic acid and at least a portion of the salt(s) of the second organic acid, if present, to form a second dispersion system comprising nanoparticles dispersed in the long-chain hydrocarbon solvent, and the nanoparticles comprise kernels, and the kernels comprise M1, optionally M2, optionally M3, oxygen, optionally sulfur, and optionally phosphorus;
   (Ic) separating the nanoparticles from the second dispersion system; and
   (Id) dispersing the nanoparticles separated in (Ic) in the liquid medium to form the nanoparticle dispersion.

19. The process of claim 18, wherein the nanoparticles have an average particle size in a range from 4 to 20 nm, and a particle size distribution of no greater than 20%.

20. The process of claim 18, wherein steps (Ia), (Ib), (Ic), and (Id) are performed in the same vessel.

21. The process of claim 18, wherein the second organic acid has a boiling point lower than the first temperature.

22. The process of claim 18, wherein the first dispersion system is substantially free of a surfactant other than the salt(s) of the long-chain organic acid.

23. The process of claim 18, wherein the second temperature is in a range from 210° C. to 450° C.

24. The process of claim 18, wherein the long-chain organic acid and the long-chain hydrocarbon solvent do not differ in number of average carbon atoms per molecule by more than 4.

* * * * *